United States Patent
Igarashi et al.

(10) Patent No.: US 10,960,128 B2
(45) Date of Patent: Mar. 30, 2021

(54) BIOLOGICAL COMPONENT COLLECTION SYSTEM AND CIRCUIT INTERNAL PRESSURE ACQUISITION METHOD

(71) Applicant: TERUMO KABUSHIKI KAISHA, Tokyo (JP)

(72) Inventors: Masatsugu Igarashi, Shizuoka (JP); Davis Benz, Lakewood, CO (US)

(73) Assignee: Terumo Kabushiki Kaisha, Tokyo (JP)

(*) Notice: Subject to any disclaimer, the term of this patent is extended or adjusted under 35 U.S.C. 154(b) by 0 days.

(21) Appl. No.: 16/668,435

(22) Filed: Oct. 30, 2019

(65) Prior Publication Data

US 2020/0164137 A1    May 28, 2020

(30) Foreign Application Priority Data

Nov. 1, 2018  (JP) .............................. JP2018-206648

(51) Int. Cl.
| | |
|---|---|
| *A61M 1/38* | (2006.01) |
| *A61M 1/36* | (2006.01) |
| *B04B 13/00* | (2006.01) |
| *G16H 20/40* | (2018.01) |
| *B04B 5/04* | (2006.01) |

(52) U.S. Cl.
CPC ............ *A61M 1/38* (2013.01); *A61M 1/3693* (2013.01); *B04B 5/0442* (2013.01); *B04B 13/00* (2013.01); *G16H 20/40* (2018.01); *A61M 2205/3331* (2013.01); *A61M 2205/3368* (2013.01)

(58) Field of Classification Search
USPC .......... 604/6.01, 4.01, 5.01; 422/44; 494/10, 494/35; 210/782, 787, 361
See application file for complete search history.

(56) References Cited

U.S. PATENT DOCUMENTS

| | | |
|---|---|---|
| 2002/0107468 A1 | 8/2002 | Chevallet et al. |
| 2011/0152055 A1 | 6/2011 | Pittinger et al. |

FOREIGN PATENT DOCUMENTS

| | | |
|---|---|---|
| EP | 0214803 A2 | 3/1987 |
| WO | 2008121120 A1 | 10/2008 |
| WO | 2011084348 A2 | 7/2011 |
| WO | 2014105755 A1 | 7/2014 |

OTHER PUBLICATIONS

International Search Report and Written Opinion, PCT/JP2019/041299, dated Jan. 23, 2020, 16 pages.

*Primary Examiner* — Walter D. Griffin
*Assistant Examiner* — Shuyi S. Liu
(74) *Attorney, Agent, or Firm* — Terumo BCT, Inc. IP Law Dept.

(57) ABSTRACT

A biological component collection system and a circuit internal pressure acquisition method are provided, which are capable of accurately measuring the circuit internal pressure. A centrifugal separation device of a blood component collection system has a first load detecting unit, an internal pressure calculation unit that calculates an internal pressure using the load detected by the first load detecting unit and internal pressure calculation data. The internal pressure calculation unit performs a calculation reflecting a change in the internal pressure calculation data depending on temperature.

13 Claims, 19 Drawing Sheets

BIOLOGICAL COMPONENT COLLECTION SYSTEM AND CIRCUIT INTERNAL PRESSURE ACQUISITION METHOD

TECHNICAL FIELD

The present invention relates to a biological component collection system equipped with a biological component collection device configured to be attachable to a separation device, as well as to a circuit internal pressure acquisition method.

BACKGROUND ART

In blood donation in recent years, in addition to whole blood collection in which whole blood is collected from blood donors, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining components are returned again into the donor's body.

In Patent Document 1, a blood component collection system is disclosed in which blood platelets are collected by centrifugally separating whole blood that is extracted from a blood donor. Such a blood component collection system comprises a blood collection circuit set, which forms a circuit through which blood or blood components to be treated flow, and a centrifugal separation device (blood component separation device) in which the blood collection circuit set is mounted.

The blood collection circuit set is equipped with a plurality of bags for accommodating a blood collection line having a blood collection needle, a band-shaped channel (separator) into which whole blood is introduced, and the blood components, etc., and a cassette connected through a plurality of tubes to the bags. A plurality of flow paths, including a line for introducing blood from a blood donor, a line for transferring the blood components into a bag, a blood returning line for returning uncollected blood components to the donor, etc., are formed in the cassette. When used, the cassette is mounted in a mounting unit disposed in the blood component separation device.

PRIOR ART DOCUMENTS

Patent Documents

Patent Document 1
Published Japanese Translation of PCT International Application No. 2013-514863 (WO2011/084348).

SUMMARY OF INVENTION

Problems the Invention Aims to Solve

In such a blood component collection system, in order to ascertain whether or not the blood component separation device is operating properly, it is necessary to measure and monitor the pressure (circuit internal pressure) inside the blood collection circuit. Similar problems also occur in biological component collection systems other than blood component collection systems.

The present invention has been devised taking into consideration the aforementioned problems, and has the object of providing a biological component collection system and a circuit internal pressure acquisition method, which are capable of accurately measuring the circuit internal pressure.

Means for Solving the Problem

A first aspect of the present invention relates to a biological component collection system equipped with a separation device adapted to separate a biological component from a biological liquid, and a biological component collection device configured to be attachable to the separation device and collect a desired biological component from the biological liquid, wherein the biological component collection device includes a line forming member made of a soft material, and forming a biological liquid line through which the biological liquid or the biological component flows, the separation device comprising a load detecting unit adapted to detect a load applied to an applied load measurement unit which partially makes up the line forming member in a device attached state in which the biological component collection device is attached to the separation device, and an internal pressure calculation unit adapted to calculate an internal pressure of the applied load measurement unit, using the load detected by the load detecting unit and the internal pressure calculation data, during collection of the biological component in which the biological liquid or the biological component is made to flow through the biological liquid line in the device attached state, wherein the internal pressure calculation data is data indicative of a relationship between the load detected by the load detecting unit and the internal pressure of the applied load measurement unit, and when calculating the internal pressure of the applied load measurement unit, the internal pressure calculation unit performs a calculation reflecting a change in the internal pressure calculation data depending on temperature.

A second aspect of the present invention relates to a biological component collection system equipped with a separation device adapted to separate a biological component from a biological liquid, and a biological component collection device configured to be attachable to the separation device and collect a desired biological component from the biological liquid, the biological component collection device comprising a line forming member made of a soft material, and forming a biological liquid line through which the biological liquid or the biological component flows, and a temperature measured section in which a temperature on the line forming member is measured, the separation device comprising a load detecting unit adapted to detect a load applied to an applied load measurement unit which partially makes up the line forming member in a device attached state in which the biological component collection device is attached to the separation device, a temperature acquisition unit adapted to acquire the temperature of the temperature measured section, a correction unit adapted to correct internal pressure calculation data indicative of a relationship between the load detected by the load detecting unit and the internal pressure of the applied load measurement unit on the basis of the temperature acquired by the temperature acquisition unit, and an internal pressure calculation unit adapted to calculate an internal pressure of the applied load measurement unit using the load detected by the load detecting unit and the internal pressure calculation data that was corrected by the correction unit, during collection of the biological component in which the biological liquid or the biological component is made to flow through the biological liquid line in the device attached state.

A third aspect of the present invention relates to a circuit internal pressure acquisition method using a biological component collection system equipped with a separation device adapted to separate a biological component from a biological liquid, and a biological component collection device configured to be attachable to the separation device and collect a desired biological component from the biological liquid, wherein the biological component collection device includes a line forming member made of a soft material, and forming a biological liquid line to allow the biological liquid or the biological component to flow therein, the circuit internal pressure acquisition method comprising a load detecting step of detecting a load applied to an applied load measurement unit which partially makes up the line forming member in a device attached state in which the biological component collection device is attached to the separation device, and an internal pressure calculation step of calculating an internal pressure of the applied load measurement unit, using the load detected by the load detecting unit and the internal pressure calculation data, during collection of the biological component by which the biological liquid or the biological component is made to flow through the biological liquid line in the device attached state, wherein the internal pressure calculation data is data indicative of a relationship between the load detected by the load detecting unit and the internal pressure of the applied load measurement unit, and in the internal pressure calculation step, a calculation is performed reflecting a change in the internal pressure calculation data depending on temperature.

Effects of the Invention

According to the present invention, since a calculation reflecting a change in the internal pressure calculation data due to temperature is performed when calculating the internal pressure of the applied load measurement unit, it is possible for the circuit internal pressure to be accurately measured.

DESCRIPTION OF EMBODIMENTS

Preferred embodiments of a biological component collection system and a circuit internal pressure acquisition method according to the present invention will be presented and described in detail below with reference to the accompanying drawings.

First Embodiment

Figure 1:
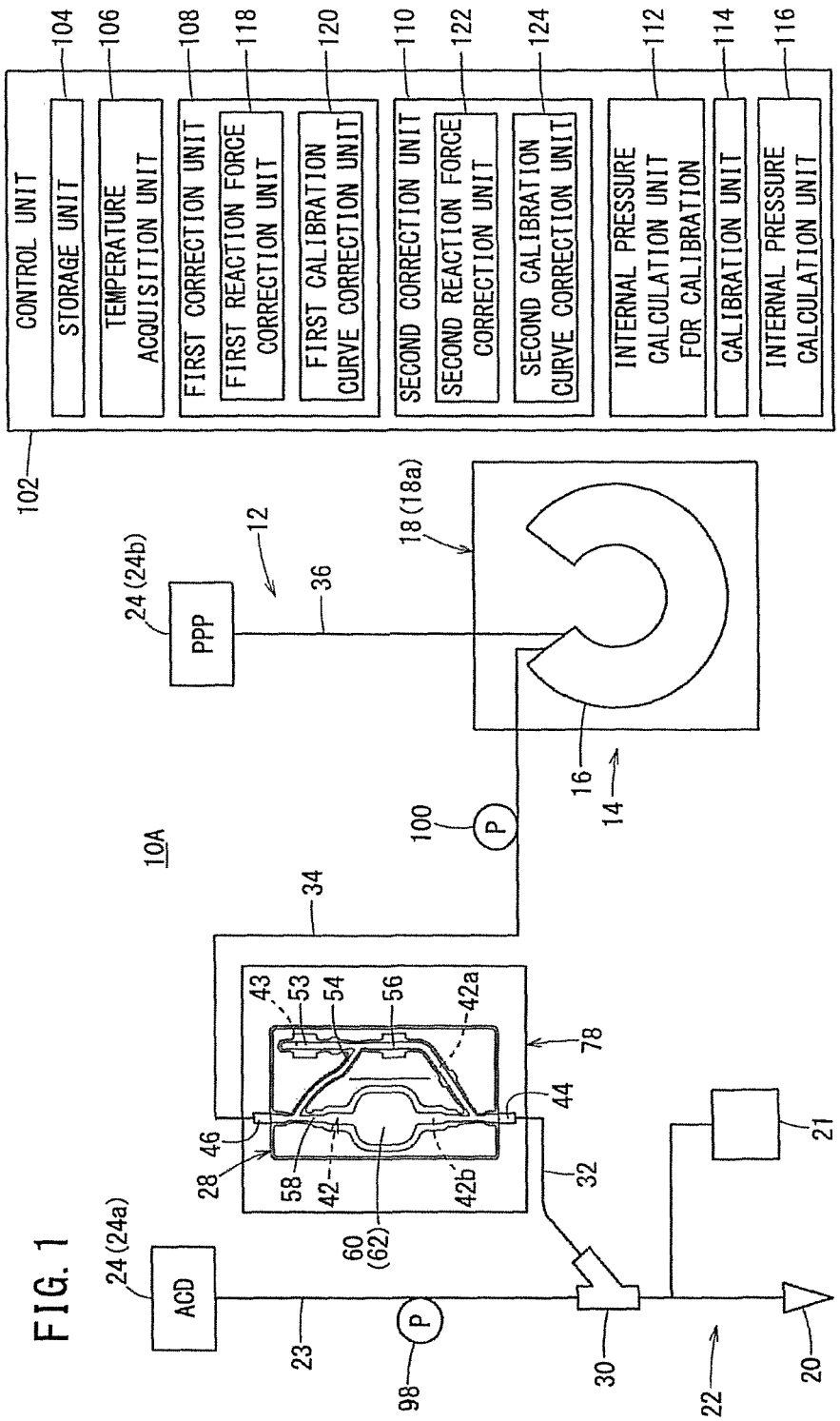
FIG. 1 is a schematic diagram of a blood component collection system according to a first embodiment of the present invention.

As shown in FIG. 1, a blood component collection system 10A, which is a first embodiment of a biological component collection system according to the present invention, is constituted as a blood apheresis system, in which blood (whole blood) is continuously extracted from a blood donor and subjected to centrifugal separation outside the body, whereby a specific blood component (in the present embodiment, plasma (platelet poor plasma: PPP)) is collected, and the remaining blood components are returned to the blood donor. In the present embodiment, the blood component is a biological component, and the blood is a biological liquid (a liquid containing at least one biological component).

First, an outline description will be given of the blood component collection system 10A shown in FIG. 1. The blood component collection system 10A is equipped with a blood collection circuit set 12 for enabling storage and flow of blood components therein, and a centrifugal separation device 14 (separation device) that applies a centrifugal force to the blood collection circuit set 12. The blood collection circuit set 12 includes a blood treatment unit 16 to which there is introduced whole blood that is removed from the blood donor, and the whole blood is centrifugally separated into a plurality of blood components. The centrifugal separation device 14 is equipped with a centrifuge unit 18 having a rotor 18a for applying a centrifugal force to the blood treatment unit 16. The blood treatment unit 16 is capable of being mounted in the centrifuge unit 18.

The blood collection circuit set 12 is discarded every time that it is used in order to prevent contamination and ensure sanitation. The blood collection circuit set 12 includes a blood collecting and blood returning unit 22 having a blood collecting needle 20 and an initial flow blood collecting bag 21, a blood treatment unit 16, a plurality of bags 24, and a blood component collection cassette 28 (hereinafter referred to as a "cassette 28") serving as a biological component collection device to which the aforementioned elements are connected via tubes. The plurality of bags 24 include an ACD solution bag 24a containing an ACD solution which is an anticoagulant, and a PPP bag 24b for storing the plasma (platelet poor plasma).

The blood collecting and blood returning unit 22 is connected to the ACD solution bag 24a and the cassette 28 via a tube connector 30. The ACD solution bag 24a is connected to the tube connector 30 via an ACD solution transfer tube 23.

The cassette 28 is connected to the blood collection and blood returning unit 22 via a donor side tube 32, and is also connected to the blood treatment unit 16 via a treatment unit side tube 34. The blood treatment unit 16 is attached to the centrifuge unit 18 (rotor 18a) of the centrifugal separation device 14, and is configured in the form of a container in which blood can be introduced therein, flow therethrough, and flow out therefrom. The PPP bag 24b is connected to the blood treatment unit 16 via a PPP transfer tube 36.

Figure 2:
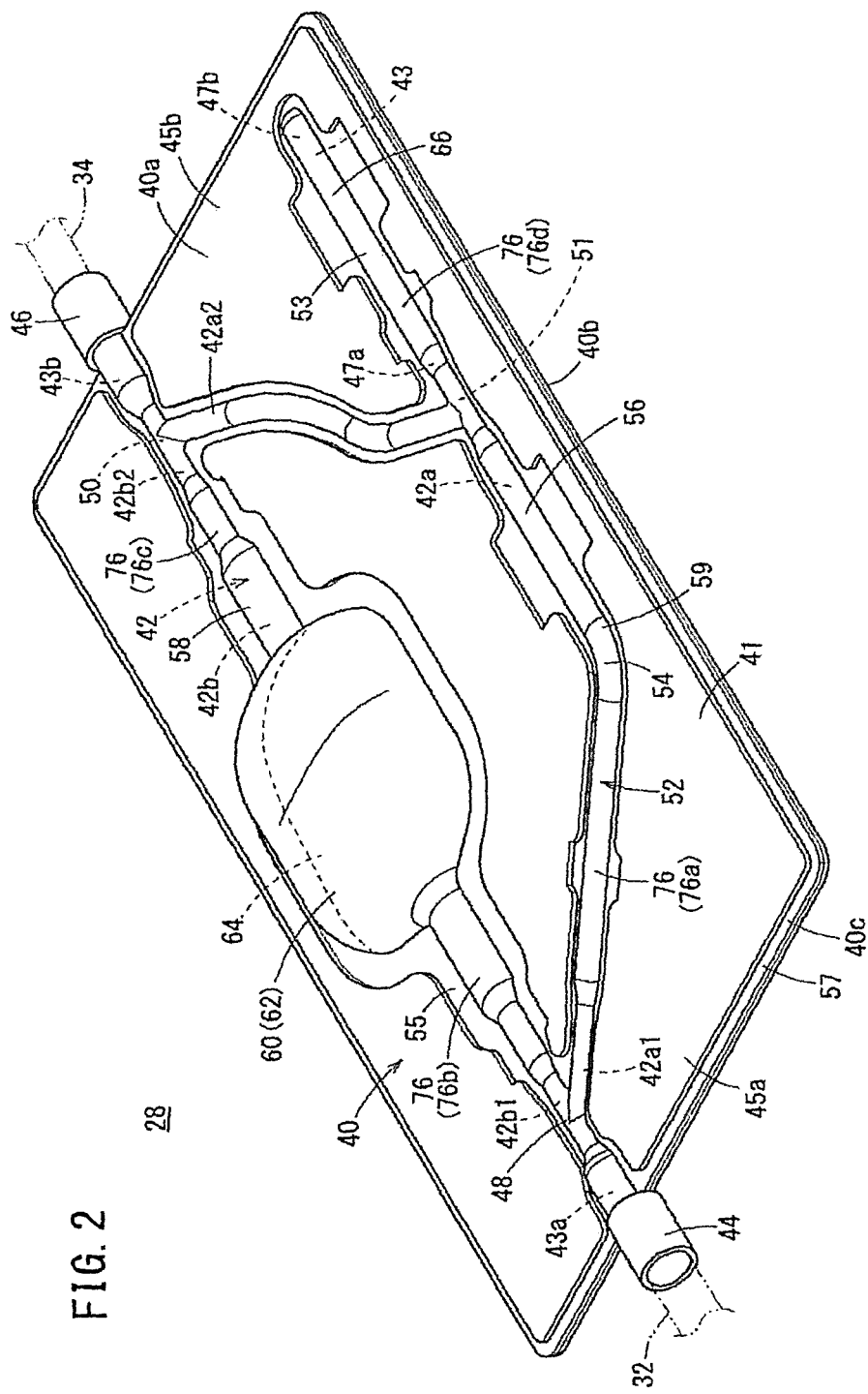
FIG. 2 is a perspective view of a blood component collection cassette shown in FIG. 1.

As shown in FIG. 2, the cassette 28 is provided with a cassette body 40 which is configured in a rectangular shape as viewed in plan. The cassette body 40 is formed of a soft material. For the soft material that constitutes the cassette body 40, the same material is used over the entirety of the cassette body 40. Moreover, the cassette body 40 may be constituted from a plurality of different materials. More specifically, the cassette body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

The cassette body 40 includes a blood line 42 (biological liquid line) and a hollow portion 43 formed between the first sheet 40a and the second sheet 40b. In the present embodiment, fusion bonding (high frequency fusion bonding, thermal fusion bonding, etc.) is used as the means for joining the first sheet 40a and the second sheet 40b. The first sheet 40a and the second sheet 40b may also be joined together by another joining means (adhesion or the like). Further, a first port member 44 and a second port member 46, which are made of a hard material (for example, polypropylene, polycarbonate, or the like), are disposed on an outer peripheral edge portion 40c of the cassette body 40.

The first port member 44 is provided at a first end portion 45a, which is one longitudinal end portion of the rectangular cassette body 40, and is connected to a first port 43a provided on one end side of the blood line 42. The second port member 46 is provided at a second end portion 45b, which is another longitudinal end portion of the cassette body 40, and is connected to a second port 43b provided on the other end side of the blood line 42. The donor side tube 32 is connected to the first port member 44, and the treatment unit side tube 34 is connected to the second port member 46.

According to the present embodiment, the first port member 44 and the second port member 46 are arranged on the same straight line along the longitudinal direction of the rectangular cassette body 40. Moreover, the first port member 44 and the second port member 46 need not necessarily be arranged on the same straight line.

The blood line 42 which is formed in the cassette body 40 includes a blood collection line 42a (collection line) through which the blood is made to flow at a time of blood collection, and a blood returning line 42b (returning line) through which the blood components are made to flow at a time that the blood is returned. One end portion 42a1 of the blood collection line 42a and one end portion 42b1 of the blood returning line 42b are connected mutually via a first coupling member 48. Another end portion 42a2 of the blood collection line 42a and another end portion 42b2 of the blood returning line 42b are connected mutually via a second coupling member 50.

Blood and blood components do not flow through the hollow portion 43 during operation of the centrifugal separation device 14. A first end portion 47a of the hollow portion 43 is connected to an intermediate part of the blood collection line 42a via a third coupling member 51. A second end portion 47b of the hollow portion 43 is closed. The blood collection line 42a and the blood returning line 42b extend at least partially in parallel with each other. The hollow portion 43 is formed in a straight line shape, and is connected in series to a portion of the blood collection line 42a that extends in parallel with the blood returning line 42b. At least a part of the blood collection line 42a extends between the hollow portion 43 and the blood returning line 42b, which extend in parallel. The first coupling member 48, the second coupling member 50, and the third coupling member 51 each constitute a portion of the blood line 42.

In the cassette body 40, sealed portions 55 in the form of fusion-bonded locations are formed along the blood line 42 on both sides of the blood line 42. Further, a sealed portion 57 is formed along the outer peripheral edge portion 40c, on the outer peripheral edge portion 40c of the cassette body 40.

In the cassette body 40 (excluding the convex portion that forms the blood line 42), locations other than the sealed portions 55 and 57 are non-sealed portions where the first sheet 40a and the second sheet 40b are not fusion bonded to each other. Since the sealed portions 55 are subject to pressure during formation thereof, the sealed portions 55 are smaller in thickness than the non-sealed portions, and are recessed with respect to the non-sealed portions. Stated otherwise, the non-sealed portions protrude in the thickness direction with respect to the sealed portions 55.

In the cassette body 40, even when there is no positive pressure acting within the blood line 42, the wall portions that form the blood line 42 bulge in convex shapes in the thickness direction of the cassette 28 on both side surfaces of the cassette body 40. Accordingly, the blood line 42 is a flow path which is opened in its natural state. When pressed by an external force, the wall portions can be elastically deformed in directions to close the blood line 42 at the pressed locations thereof.

The cassette body 40 comprises a line forming member 52 that forms the blood line 42, and a hollow portion forming member 53 that forms the hollow portion 43. The line forming member 52 includes a blood collection line forming member 54 that forms the blood collection line 42a. In the blood collection line forming member 54, in a cassette attached state (device attached state) in which the cassette 28 is attached to the centrifugal separation device 14, a first applied load measurement unit 56 (first pressed portion) is provided, which is pressed by a later-described first load detecting unit 88 (see FIG. 3) that is installed in the centrifugal separation device 14. The first applied load measurement unit 56 constitutes a part of the wall portions of the blood collection line 42a. Accordingly, the first applied load measurement unit 56 bulges out in the thickness direction of the cassette body 40 from a sheet surface 41 (base surface) of the cassette body 40.

Figure 3:
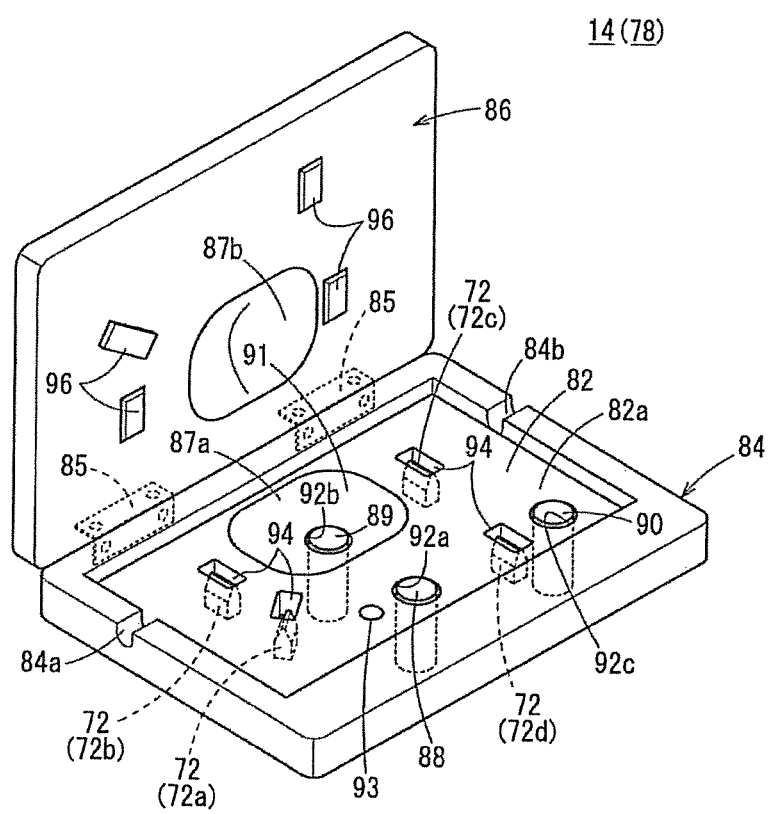
FIG. 3 is a perspective view of a cassette mounting unit shown in FIG. 1.

In the vicinity of the first applied load measurement unit 56 within the blood collection line forming member 54, there is provided a temperature measured section 59, the temperature of which is measured by a temperature measurement unit 93 (see FIG. 3). In this case, by measuring the temperature of the temperature measured section 59 with the temperature measurement unit 93, it is possible to accurately acquire the temperature of the first applied load measurement unit 56. Moreover, the temperature measured section 59 can be provided at any arbitrary position of the line forming member 52, insofar as it is a portion where the temperature on the line forming member 52 is measured. Stated otherwise, the temperature measured section 59 may be formed by at least a portion of the first applied load measurement unit 56. In this case, it is possible to more accurately acquire the temperature of the first applied load measurement unit 56. Further, the temperature measured section 59 may also be provided in a blood returning line forming member 58 to be described later.

The line forming member 52 includes a blood returning line forming member 58 that forms the blood returning line 42b. In the blood returning line forming member 58, in the cassette attached state, a second applied load measurement unit 60 (second pressed portion, applied load measurement unit for calibration) is provided, which is pressed by a later-described second load detecting unit 89 (see FIG. 3) that is installed in the centrifugal separation device 14. The second applied load measurement unit 60 constitutes a part of the wall portions of the blood returning line 42b. Accordingly, the second applied load measurement unit 60 bulges out in the thickness direction of the cassette body 40 from a sheet surface 41 of the cassette body 40.

The second applied load measurement unit 60 constitutes a filter accommodating unit 62. The filter accommodating unit 62 accommodates a filter member 64 for separating predetermined components (clotted blood or blood clumps) contained within the blood components.

The second applied load measurement unit 60 is more easily deformable than the first applied load measurement unit 56. In the present embodiment, the width of the second applied load measurement unit 60 is greater than the width of the first applied load measurement unit 56, whereby the second applied load measurement unit 60 is more easily deformable than the first applied load measurement unit 56. The ratio of the width of the second applied load measurement unit 60 with respect to the width of the first applied load measurement unit 56 is set, for example, to 300% or greater, preferably is set to 500% or greater, and more preferably, is set to 800% or greater.

Moreover, the width of the wall portion that constitutes the second applied load measurement unit 60 may be set to be thinner than the width of the wall portion of the first applied load measurement unit 56, whereby the second applied load measurement unit 60 may be more easily deformable than the first applied load measurement unit 56. Alternatively, the second applied load measurement unit 60 may be made of a material that is softer than that of the first applied load measurement unit 56, whereby the second applied load measurement unit 60 may be more easily deformable than the first applied load measurement unit 56.

The hollow portion forming member 53 includes a third applied load measurement unit 66 (reaction force measurement unit) made of a soft material. In the cassette attached state, the third applied load measurement unit 66 is a site that is pressed by a later-described third load detecting unit 90 which is installed in the centrifugal separation device 14.

The first applied load measurement unit 56 and the third applied load measurement unit 66 are formed to have the same shape and the same size as each other. Accordingly, the rigidities of the first applied load measurement unit 56 and the third applied load measurement unit 66 are mutually the same.

On the cassette 28, there are provided a plurality of clamp action members 76 (76a to 76d) on which a plurality of clamps 72 (72a to 72d) (see FIG. 3), which act as flow path opening/closing mechanisms, are provided in the centrifugal separation device 14. When the cassette 28 is installed in the centrifugal separation device 14, the clamp action members 76 abut against or are placed in facing relation to their corresponding clamps 72. More specifically, the clamp action member 76a is disposed at a location forming a side of the first port member 44 of the blood collection line 42a in the cassette 28. The clamp action members 76b, 76c are disposed respectively at locations forming both sides of the second applied load measurement unit 60 within the blood returning line 42b. The clamp action member 76d is disposed between the third applied load measurement unit 66 and the third coupling member 51 (at a location of the hollow portion 43 in the vicinity of the third coupling member 51).

Moreover, the flow path structure formed in the cassette 28, and the number and arrangement of the bags 24 that are provided are not limited to the configurations shown and described above, but may be modified in accordance with the type of blood components to be collected, the method of use, and the like.

In FIG. 1, the centrifugal separation device 14 is a device that is used repeatedly during blood component collection, and is provided, for example, in a medical facility, a blood collection vehicle, or the like. The centrifugal separation device 14 is equipped with the centrifuge unit 18 having the rotor 18a, and a cassette mounting unit 78 configured in a manner so that the cassette 28 of the blood collection circuit set 12 is capable of being attached thereto.

As shown in FIG. 3, the cassette mounting unit 78 includes an attachment base 84 having a cassette mounting groove 82 formed therein, a lid 86 which can be opened and closed and is configured in a manner so as to cover the attachment base 84 when closed, and a plurality of clamps 72 configured to be capable of pressing the clamp action members 76 (see FIG. 2) of the cassette 28. The cassette mounting unit 78 is further equipped with a first load detecting unit 88 which is capable of pressing the first applied load measurement unit 56 (see FIG. 2) of the cassette 28, a second load detecting unit 89 (load detecting unit for calibration) which is capable of pressing the second applied load measurement unit 60 (see FIG. 2) of the cassette 28, a third load detecting unit 90 (reaction force detecting unit) which is capable of pressing the third applied load measurement unit 66 (see FIG. 2) of the cassette 28, and the temperature measurement unit 93 that measures the temperature of the temperature measured section 59 (see FIG. 2).

A first port arrangement groove 84a into which the first port member 44 of the cassette 28 can be arranged, and a second port arrangement groove 84b into which the second port member 46 of the cassette 28 can be arranged are provided on the outer peripheral portion of the attachment base 84. The first port arrangement groove 84a and the second port arrangement groove 84b are in communication with the cassette mounting groove 82.

The lid 86 is connected in a rotatable manner to the attachment base 84 via a hinge 85. When the lid 86 is closed with the cassette 28 being held in the cassette mounting groove 82 of the attachment base 84, the cassette 28 is sandwiched between the attachment base 84 and the lid 86. On the attachment base 84 and the lid 86, there are respectively provided concave portions 87*a*, 87*b* in which the filter accommodating unit 62 of the cassette 28 can be received. Consequently, the cassette 28 is appropriately retained between the attachment base 84 and the lid 86, while also preventing the filter accommodating unit 62 from being crushed. Further, the concave portions 87*a*, 87*b* prevent the filter accommodating unit 62 from bulging excessively.

The first load detecting unit 88 is inserted into a first through hole 92*a* provided in the attachment base 84, together with being exposed in the cassette mounting groove 82. An upper surface of the first load detecting unit 88 protrudes from a bottom surface 82*a* of the cassette mounting groove 82. The second load detecting unit 89 is inserted into a second through hole 92*b* provided in a bottom surface 91 of the concave portion 87*a*, together with being exposed in the concave portion 87*a*. An upper surface of the second load detecting unit 89 protrudes from the bottom surface 91 of the concave portion 87*a*. The third load detecting unit 90 is inserted into a third through hole 92*c* provided in the attachment base 84, together with being exposed in the cassette mounting groove 82. An upper surface of the third load detecting unit 90 protrudes from the bottom surface 82*a* of the cassette mounting groove 82.

The protruding height of the first load detecting unit 88 from the bottom surface 82*a* is the same as the protruding height of the third load detecting unit 90 from the bottom surface 82*a*. The first load detecting unit 88, the second load detecting unit 89, and the third load detecting unit 90 are constituted from load cells, for example. The temperature measurement unit 93 is position in the vicinity of the first load detecting unit 88.

The plurality of clamps 72 (72*a* to 72*d*) are capable of being advanced and retracted in the cassette thickness direction in a state in which the cassette 28 is retained in the cassette mounting groove 82, and are disposed corresponding to the arrangement of the plurality of clamp action members 76 (76*a* to 76*d*) provided on the cassette 28. The plurality of clamps 72 are capable of pressing the plurality of clamp action members 76, respectively, via a plurality of holes 94 that open on a bottom surface 82*a* of the cassette mounting groove 82. When closed, a plurality of projections 96 are provided on the lid 86 at positions corresponding to the plurality of holes 94 (clamps 72).

At a time that the clamp action members 76 are not being pressed by the clamps 72, in a state in which the cassette 28 is mounted in the cassette mounting unit 78, the flow paths inside the clamp action members 76 are opened. When the clamps 72 protrude from the holes 94 and press the clamp action members 76, the flow paths inside the clamp action members 76 are closed. In addition, when the clamps 72 are retracted, due to the elastic restorative force of (the clamp action members 76 of) the cassette body 40, the clamp action members 76 are restored to their original shape, and the flow paths inside the clamp action members 76 are opened.

As shown in FIG. 1, the centrifugal separation device 14 includes an ACD solution transfer pump 98 which acts on the ACD solution transfer tube 23, and a collection and returning pump 100 which acts on the treatment unit side tube 34 that is connected to the cassette 28. The ACD solution transfer pump 98 is a pump that transfers the ACD solution from the ACD solution bag 24*a* to the cassette 28 and the blood treatment unit 16 via the ACD solution transfer tube 23. The collection and returning pump 100 is a pump for transferring the blood or blood components. Stated otherwise, the collection and returning pump 100 is a pump that transfers blood from the blood donor to the blood treatment unit 16, and together therewith, transfers the blood from the blood treatment unit 16 back to the blood donor. The ACD solution transfer pump 98 and the collection and returning pump 100 are constituted, for example, by a roller pump or a finger pump.

The centrifugal separation device 14 further includes a control unit 102. The control unit 102 is a computation device including a microcomputer, and has a CPU (central processing unit), and a ROM, a RAM, etc., serving as memories, wherein by reading out and executing programs stored in the ROM, the CPU functions as various function realizing units (function realizing means). Moreover, the various function realizing units may be constituted by function realizing devices in the form of hardware.

The control unit 102 controls operations of the above-described plurality of clamps 72. The control unit 102 comprises a storage unit 104, a temperature acquisition unit 106 (information acquisition unit), a first correction unit 108, a second correction unit 110, an internal pressure calculation unit for calibration 112, a calibration unit 114, and an internal pressure calculation unit 116.

The temperature acquisition unit 106 acquires the temperature of the line forming member 52 (influence information that exerts an influence on the reaction force of the first applied load measurement unit 56). More specifically, the temperature acquisition unit 106 acquires the temperature measured by the temperature measurement unit 93.

Figure 11A:
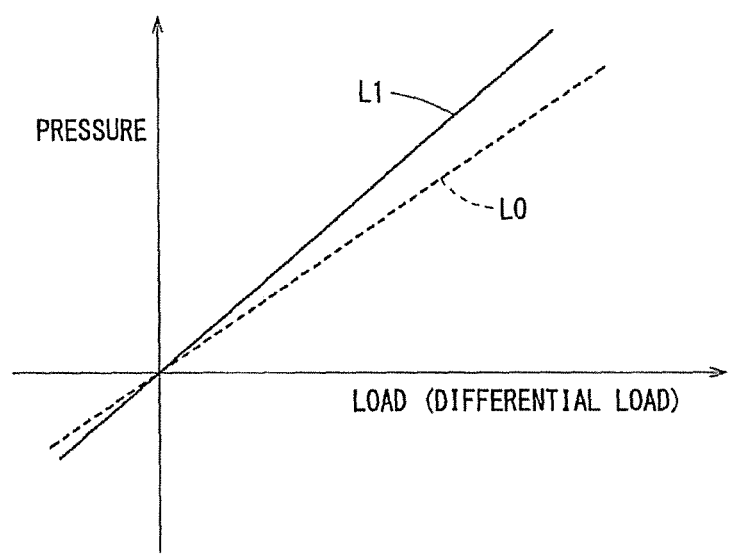
FIG. 11A is an explanatory diagram of correction of a calibration curve used for calibration.

On the basis of the temperature acquired by the temperature acquisition unit 106, the first correction unit 108 calculates internal pressure calculation data for calibration, which is indicative of a relationship between the load detected by the second load detecting unit 89 and the internal pressure of the second applied load measurement unit 60. The internal pressure calculation data for calibration is data including a reaction force based on an elastic restorative force of the second applied load measurement unit 60, and a calibration curve L0 used for calibration (see FIG. 11A) indicative of a relationship between a differential load, which is obtained by subtracting the reaction force of the second applied load measurement unit 60 from the load detected by the second load detecting unit 89, and the internal pressure of the second applied load measurement unit 60.

The first correction unit 108 includes a first reaction force correction unit 118 that corrects the reaction force of the second applied load measurement unit 60 based on the temperature acquired by the temperature acquisition unit 106, and a first calibration curve correction unit 120 that corrects the calibration curve L0 used for calibration based on the temperature acquired by the temperature acquisition unit 106.

On the basis of the temperature acquired by the temperature acquisition unit 106, the second correction unit 110 calculates internal pressure calculation data, which is indicative of a relationship between the load detected by the first load detecting unit 88 and the internal pressure of the first applied load measurement unit 56. The internal pressure calculation data is data including a reaction force based on an elastic restorative force of the first applied load measurement unit 56, and a calibration curve La (see FIG. 11B) indicative of a relationship between a differential load, which is obtained by subtracting the reaction force of the first applied load measurement unit 56 from the load detected by the first load detecting unit 88, and the internal pressure of the first applied load measurement unit 56.

The second correction unit 110 includes a second reaction force correction unit 122 that corrects the load (the reaction force based on the restorative force of the third applied load measurement unit 66) detected by the third load detecting unit 90 using the temperature acquired by the temperature acquisition unit 106, and a second calibration curve correction unit 124 that corrects the calibration curve La based on the temperature acquired by the temperature acquisition unit 106.

In the cassette attached state, before collection of blood components is performed, the internal pressure calculation unit for calibration 112 calculates the internal pressure of the second applied load measurement unit 60 using the load detected by the second load detecting unit 89, and the internal pressure calculation data for calibration which is corrected by the first correction unit 108. More specifically, the internal pressure calculation unit for calibration 112 carries out a calculation that reflects a change in the internal pressure calculation data for calibration due to temperature.

The calibration unit 114 calibrates the internal pressure calculation data (slope of the calibration curve L) using the internal pressure of the second applied load measurement unit 60 as calculated by the internal pressure calculation unit for calibration 112.

In the cassette attached state, during collection of the blood components, the internal pressure calculation unit 116 calculates the internal pressure (circuit internal pressure) of the first applied load measurement unit 56, using the load detected by the first load detecting unit 88, and the internal pressure calculation data which is corrected by the second correction unit 110. More specifically, the internal pressure calculation unit 116 carries out a calculation that reflects a change in the internal pressure calculation data due to temperature.

Next, operations of the blood component collection system 10A according to the present embodiment, which is configured in the manner described above, will be described.

As a preparation (set-up) for collecting blood components from a blood donor using the blood component collection system 10A shown in FIG. 1, the blood collection circuit set 12 is attached to the centrifugal separation device 14. More specifically, the cassette 28 is mounted in the cassette mounting unit 78, and the blood treatment unit 16 is attached to the rotor 18a. On the other hand, the blood collection needle 20 pierces and is inserted into the blood donor.

Figure 4:
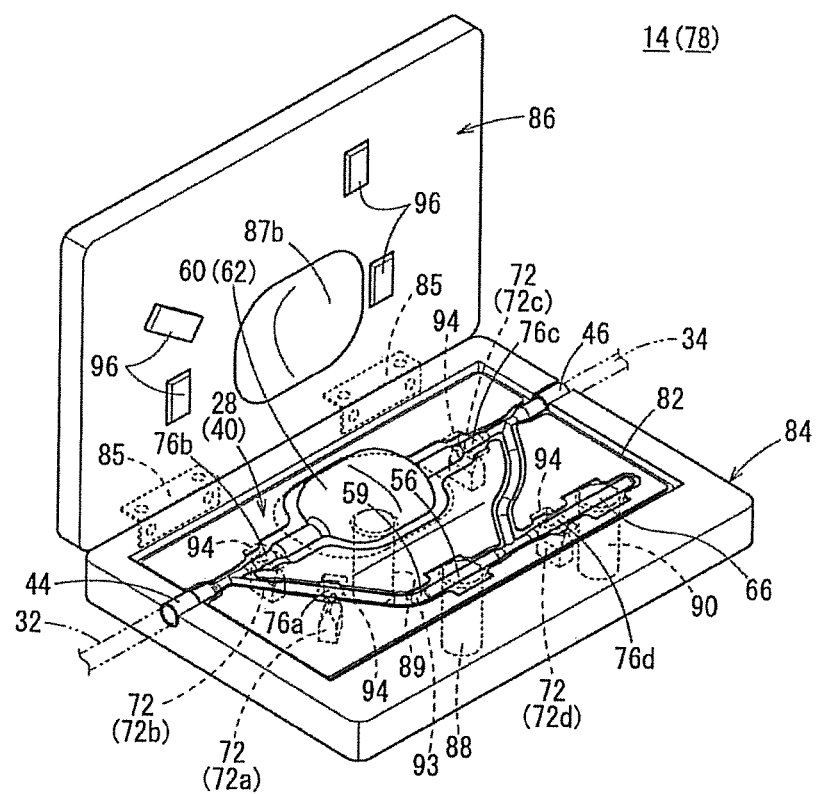
FIG. 4 is a perspective view showing a state in which the cassette of FIG. 2 is placed in the cassette mounting unit of FIG. 3.

When the cassette 28 is mounted in the cassette mounting unit 78, as shown in FIG. 4, at first, the cassette 28 is mounted in the cassette mounting groove 82. In addition, by closing the lid 86, the cassette 28 is placed in a state of being held between the lid 86 and the attachment base 84. As a result, the first applied load measurement unit 56, the second applied load measurement unit 60, and the third applied load measurement unit 66 of the cassette 28 are pressed respectively by the first load detecting unit 88, the second load detecting unit 89, and the third load detecting unit 90, and are placed in a state of being slightly elastically deformed.

In this case, the amount of deformation of the first applied load measurement unit 56 due to being pressed by the first load detecting unit 88 is the same as the amount of deformation of the third applied load measurement unit 66 due to being pressed by the third load detecting unit 90. Further, the plurality of clamp action members 76 of the cassette 28 are placed in facing relation with respect to the plurality of clamps 72.

When a command is issued by operation of a user with respect to the centrifugal separation device 14 in order to initiate operations, in the centrifugal separation device 14, after having carried out a later-described calibration step, then under the action of the ACD solution transfer pump 98, priming with the ACD solution is carried out. More specifically, at a stage at which it is detected by a non-illustrated line sensor disposed outside of the cassette 28 that the ACD solution has arrived in the immediate vicinity of the first port 43a, priming by the ACD solution is terminated.

Next, by rotating the rotor 18a, the centrifugal separation device 14 applies a centrifugal force to the blood treatment unit 16 that is attached to the rotor 18a, and together therewith, by operation of the collection and returning pump 100, blood (whole blood) from the blood donor is extracted and introduced into the blood treatment unit 16 (blood collection operation). By the centrifugal force that accompanies rotation of the rotor 18a, the blood introduced into the blood treatment unit 16 is separated into red blood cells (concentrated red blood cells), a buffy coat, and plasma (platelet poor plasma).

The plasma that is separated in the blood treatment unit 16 is introduced into the PPP bag 24b via the PPP transfer tube 36. After completion of the centrifugal separation process, the remaining blood components (the red blood cells and the buffy coat) are returned to the blood donor (returning operation). At this time, since foreign substances such as blood clumps and the like contained within the remaining blood components are trapped by the filter member 64 provided in the blood returning line 42b of the cassette 28, any risk of such foreign matter being returned to the blood donor can be reduced. The collection operation and the returning operation described above are performed a plurality of times.

During operation of the blood component collection system 10A, the clamps 72 (see FIG. 3) of the centrifugal separation device 14 are operated in the following manner.

Figure 5:
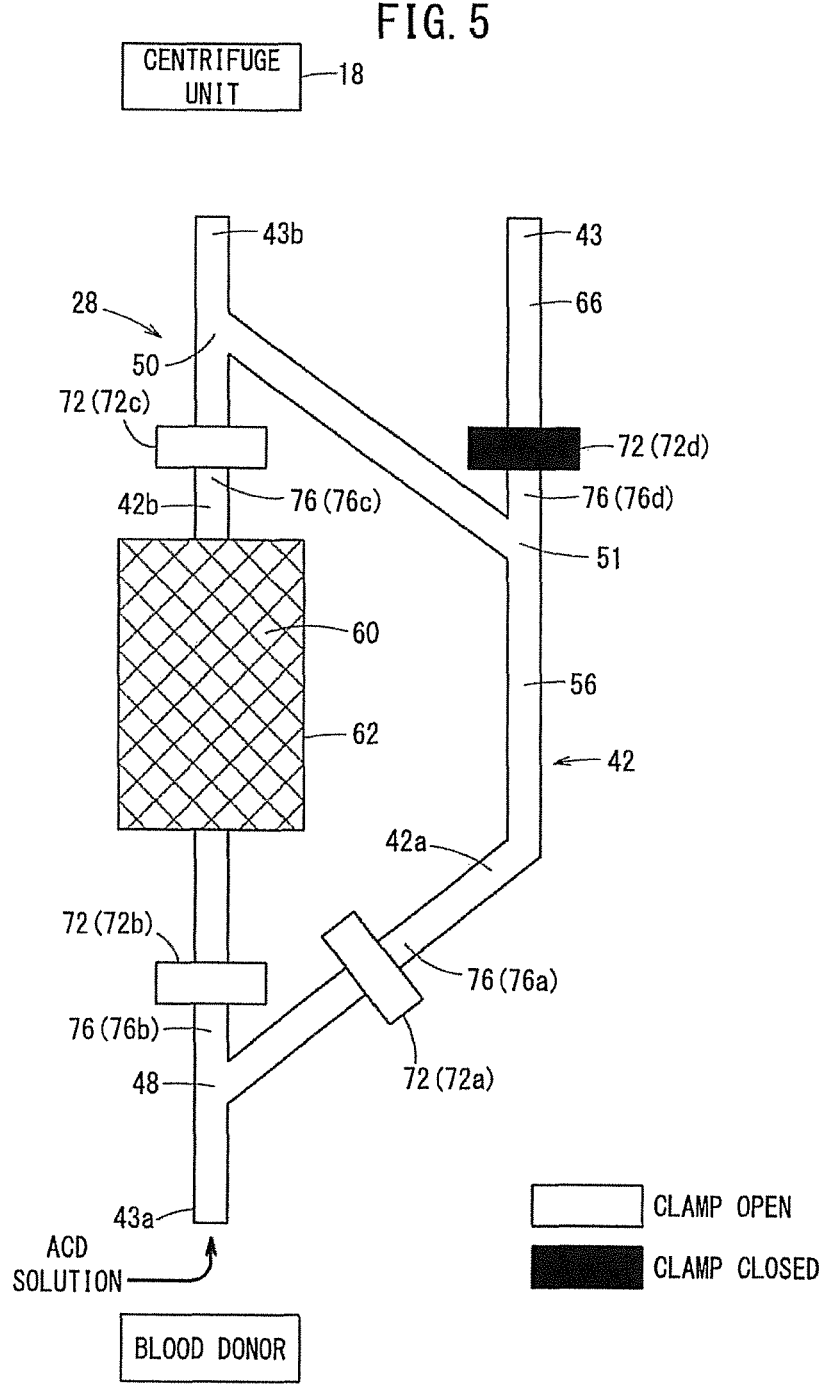
FIG. 5 is a first explanatory diagram illustrating the operation of clamps.

As shown in FIG. 5, when priming with the ACD solution is carried out, the clamp 72d is closed, and the clamps 72a, 72b, and 72c are opened. Consequently, a state is brought about in which the hollow portion 43 is cut off from other parts of the blood line 42. In addition, in this state, priming by the ACD solution is terminated at a stage at which it is detected by a non-illustrated line sensor outside the cassette 28 in the immediate vicinity of the first port 43a that the ACD solution has arrived in close proximity to the first port 43a.

Figure 6:
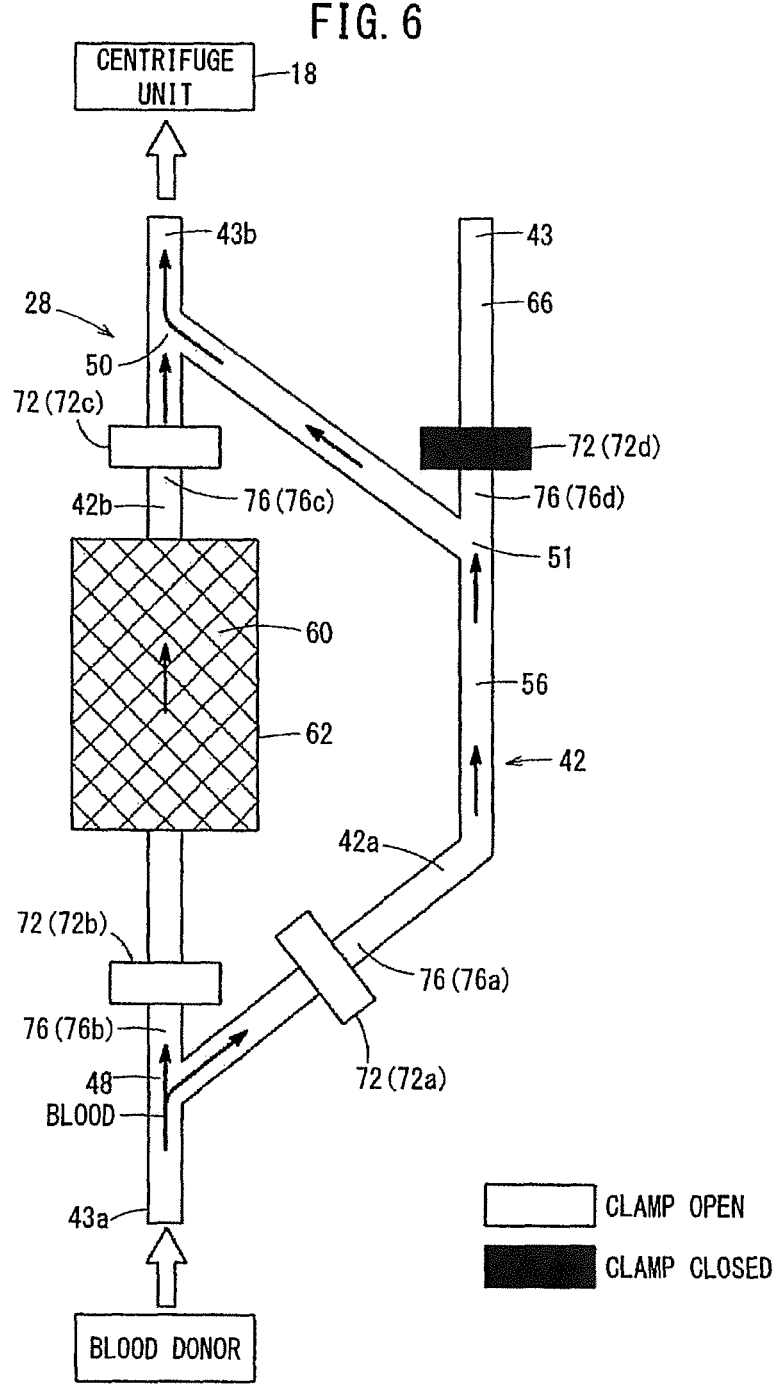
FIG. 6 is a second explanatory diagram illustrating the operation of clamps.

Next, when blood collection is performed for the first time, as shown in FIG. 6, the state in which the clamp 72d is closed and the clamps 72a, 72b, and 72c are opened is maintained. In addition, in this state, blood from the blood donor is introduced into the blood line 42 of the cassette 28, and all of the air inside the blood line 42 (circuit) of the cassette 28 is pushed out by the blood into the blood treatment unit 16.

Figure 7:
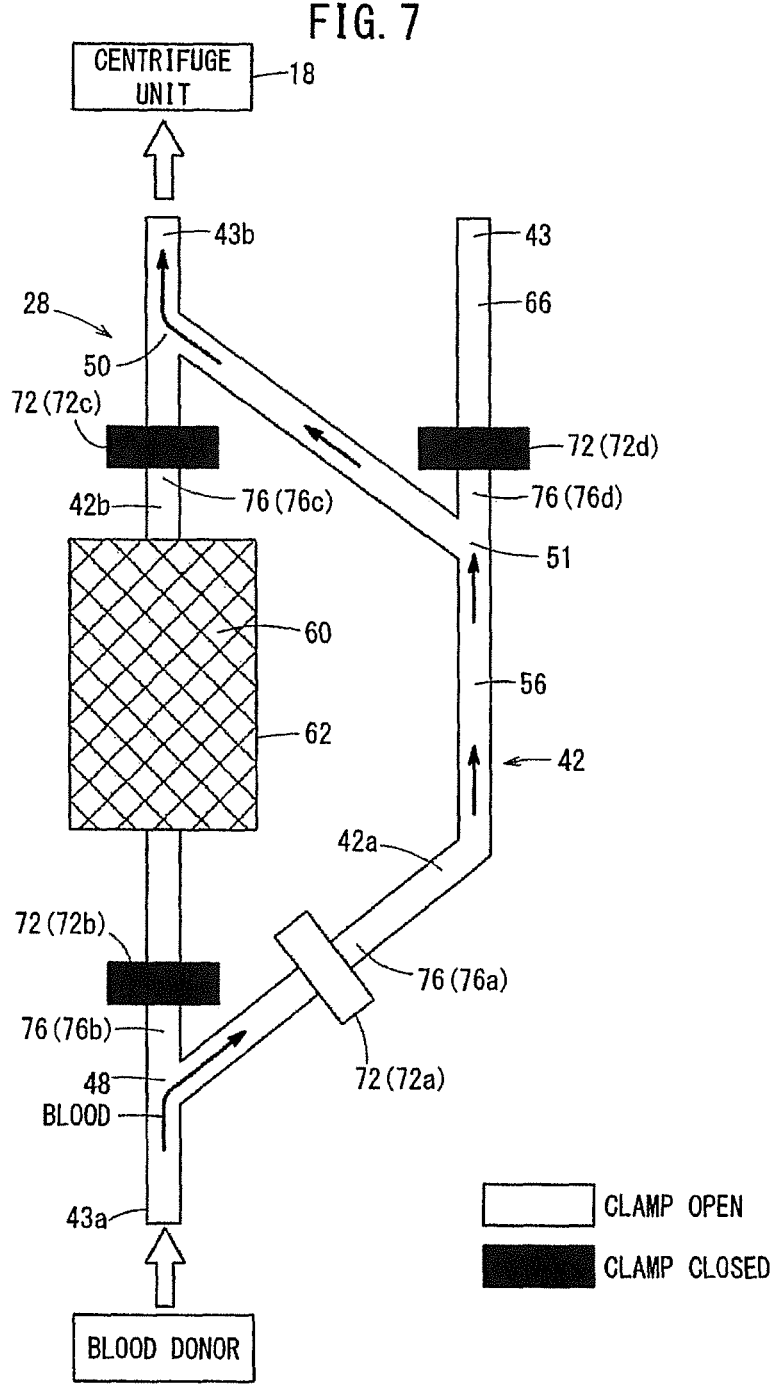
FIG. 7 is a third explanatory diagram illustrating the operation of clamps.

During the course of initial blood collection, as shown in FIG. 7, by closing the clamps 72b and 72c, the blood returning line 42b is closed. Consequently, a negative pressure is prevented from acting on the filter accommodating unit 62 and blocking the filter accommodating unit 62.

Figure 8:
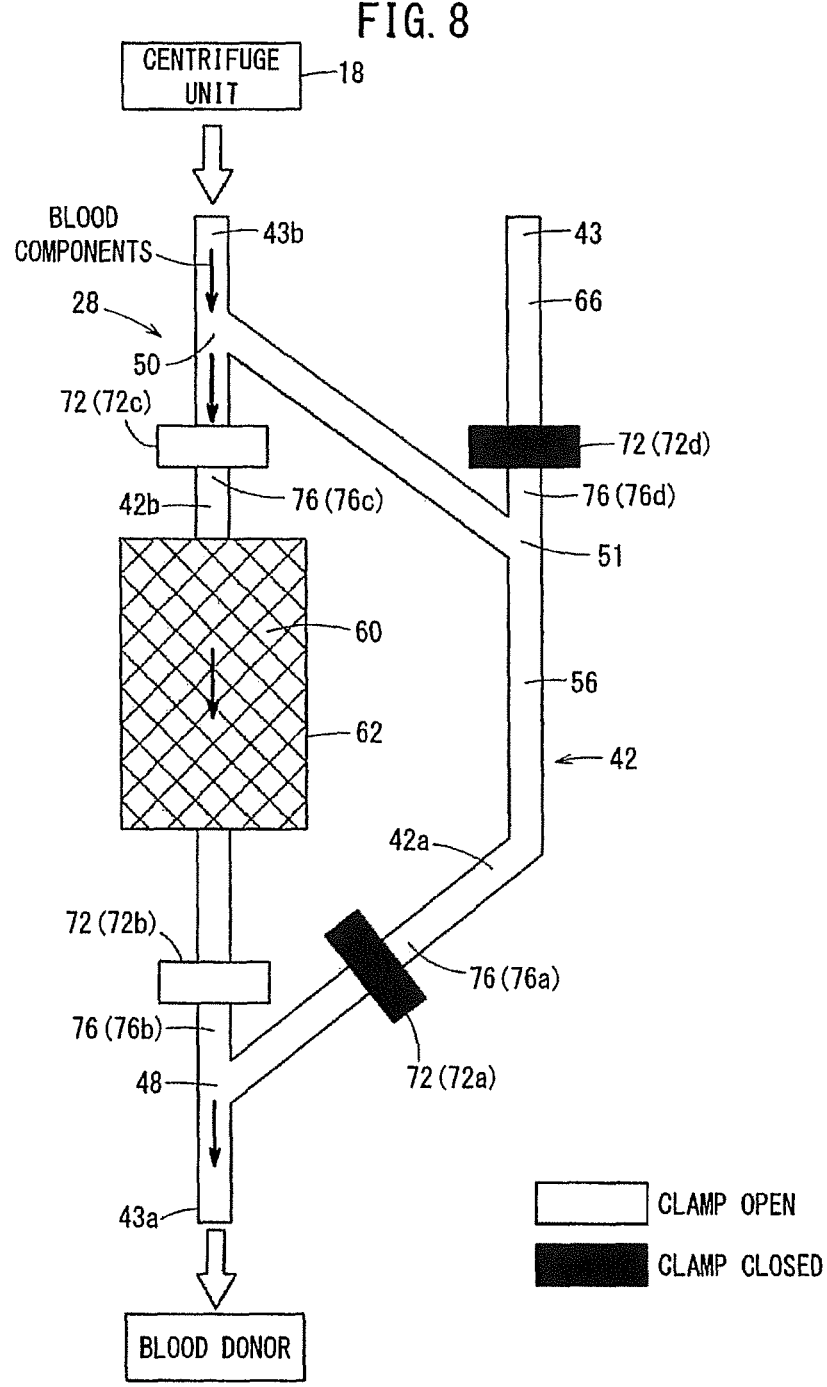
FIG. 8 is a fourth explanatory diagram illustrating the operation of clamps.

Next, when return of the blood components to the blood donor is carried out, as shown in FIG. 8, the clamp 72a is closed, and the clamps 72b and 72c are opened. Thus, the blood collection line 42a is closed, whereas the blood returning line 42b is opened. Accordingly, when the blood components pass through the filter member 64, clotted blood contained within the blood components is trapped by the filter member 64. Since the blood collection line 42a is closed, foreign matter cannot be returned to the blood donor via the blood collection line 42a.

Figure 9:
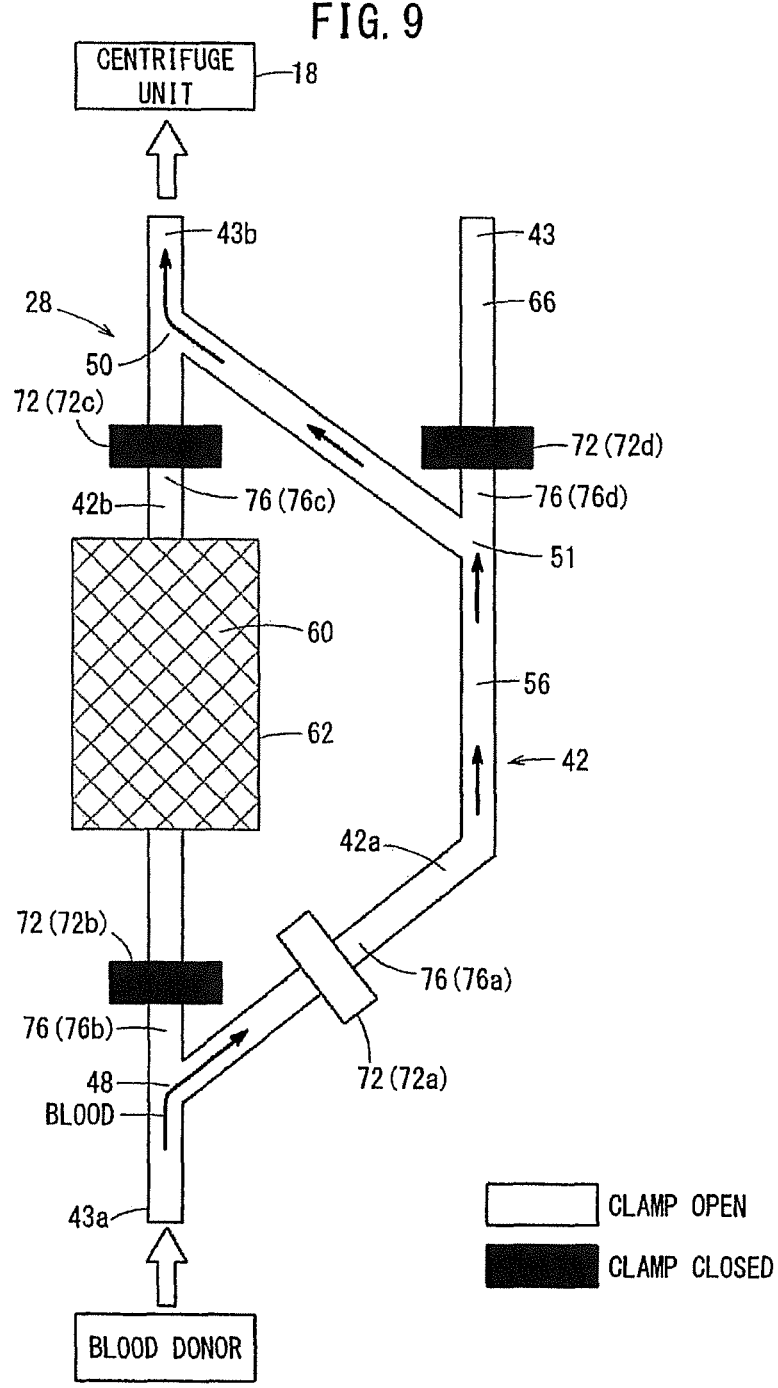
FIG. 9 is a fifth explanatory diagram illustrating the operation of clamps.

Next, when second and subsequent blood collections are carried out, as shown in FIG. 9, the clamps 72b and 72c are closed, and the clamp 72a is opened. Thus, the blood returning line 42b is closed, whereas the blood collection line 42a is opened. Accordingly, from among the blood collection line 42a and the blood returning line 42b, blood is transferred via only the blood collection line 42a to (the centrifuge unit 18 of) the blood treatment unit 16. Thereafter, return of the blood (see FIG. 8) is carried out again. Collection of blood and return of the blood in this manner are repeated a plurality of times.

In addition, when return of the blood is performed for the last time, as shown in FIG. 8, the clamp 72a is closed, and the clamps 72b and 72c are opened.

Next, a circuit internal pressure acquisition method in which the blood component collection system 10A is used will be described with reference to the flowchart shown in FIG. 10.

Figure 10:
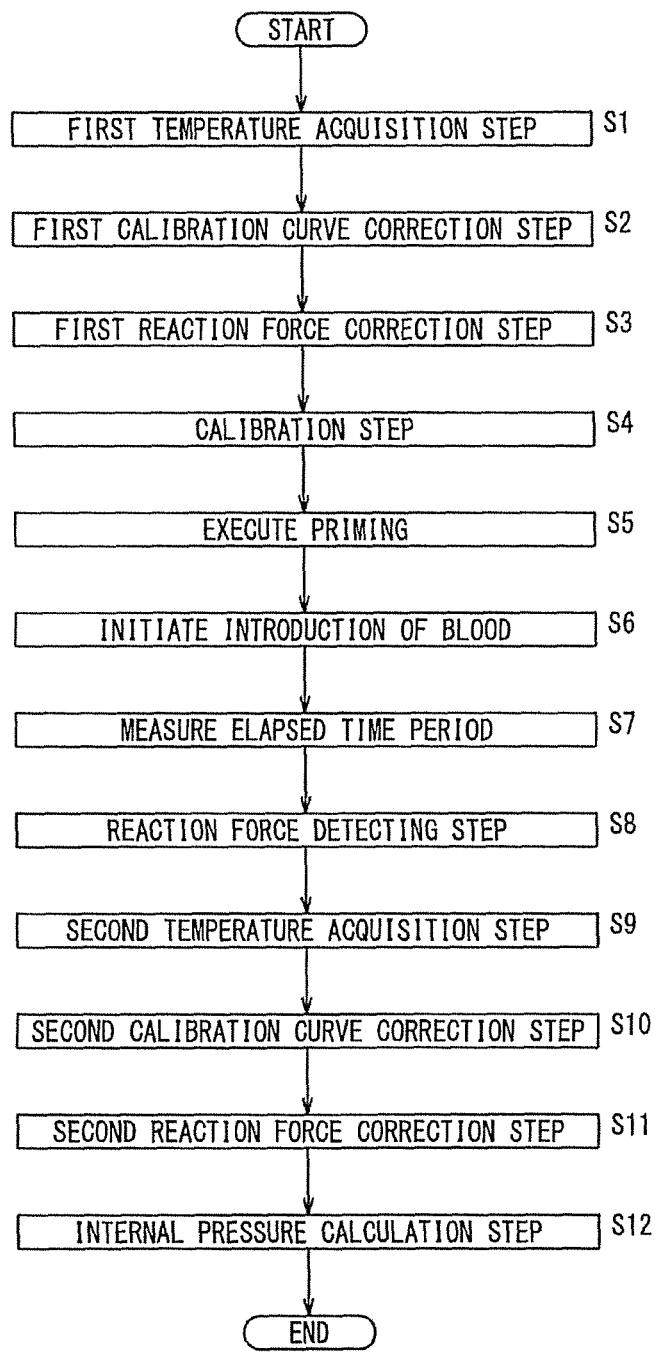
FIG. 10 is a flowchart for describing a circuit internal pressure acquisition method according to the first embodiment of the present invention.

In the circuit internal pressure acquisition method, as shown in FIG. 10, in a first temperature acquisition step of step S1, the temperature acquisition unit 106 acquires the temperature of the line forming member 52 (temperature measured section 59) which is measured by the temperature measurement unit 93.

In addition, in a first calibration curve correction step of step S2, the first calibration curve correction unit 120 corrects the slope of the calibration curve L0 used for calibration of the second applied load measurement unit 60, on the basis of the temperature acquired in the first temperature acquisition step. Consequently, a calibration curve L1 with the slope thereof corrected is obtained (see FIG. 11A). The calibration curve L0 used for calibration can be acquired in advance by experiment or analysis.

Further, in a first reaction force correction step of step S3, the first reaction force correction unit 118 corrects the reaction force on the basis of the elastic restorative force of the second applied load measurement unit 60 which is based on the temperature acquired in the first temperature acquisition step.

Subsequently, in a calibration step of step S4, the internal pressure calculation unit for calibration 112 calculates the internal pressure of the second applied load measurement unit 60 on the basis of the calibration curve L1, and a differential load, which is obtained by subtracting the reaction force of the second applied load measurement unit 60 from the load detected by the second load detecting unit 89. Additionally, the calibration unit 114 calibrates the internal pressure calculation data (slope of the calibration curve L) using the internal pressure calculated by the internal pressure calculation unit for calibration 112 (see FIG. 11B). Consequently, the calibration curve La which has been calibrated is obtained. The calibration curve L can be acquired in advance by experiment or analysis.

Since the second applied load measurement unit 60 is more easily deformed than the first applied load measurement unit 56, the relationship between the load detected by the second load detecting unit 89 and the pressure corresponding to the load is extremely stable. Accordingly, by using the second load detecting unit 89 as a reference sensor for the first load detecting unit 88, and thereby calibrating the slope of the calibration curve L used when calculating the circuit internal pressure in the correction step, it is possible to measure the circuit internal pressure with high accuracy.

Next, in step S5, priming is performed. More specifically, the ACD solution transfer tube 23 is connected to the ACD solution bag 24a, and the ACD solution transfer pump 98 is driven to thereby perform an operation to fill the ACD solution until just before the blood line 42 of the cassette 28.

Thereafter, in step S6, blood is introduced into the blood line 42 of the cassette 28. At this time, in step S7, the control unit 102 starts to measure the elapsed time period from the start of flow of blood in the blood collection line 42a.

Next, in the reaction force detecting step of step S8, in order to obtain a reaction force on the basis of elastic restorative force of the first applied load measurement unit 56, the third load detecting unit 90 detects the load applied to the third applied load measurement unit 66 (the reaction force based on the elastic restorative force of the third applied load measurement unit 66).

Further, in a second temperature acquisition step (information acquisition step) of step S9, the temperature acquisition unit 106 calculates the temperature of the line forming member 52 (first applied load measurement unit 56) on the basis of the elapsed time period and a time and temperature curve (temperature calculation data). The time and temperature curve is data indicative of a relationship between the elapsed time period since the start of introduction of blood into the blood line 42 and the temperature of the line forming member 52, and such data is saved (stored) in the storage unit 104. The time and temperature curve can be acquired in advance by experiment or analysis.

Moreover, in the second temperature acquisition step, the time and temperature curve may be referred to by accessing an external database in which the time and temperature curve is stored. Further, in the second temperature acquisition step, the temperature (temperature of the wall portion of the blood line 42) of the line forming member 52 (temperature measured section 59) may be acquired using the temperature measurement unit 93.

Figure 11B:
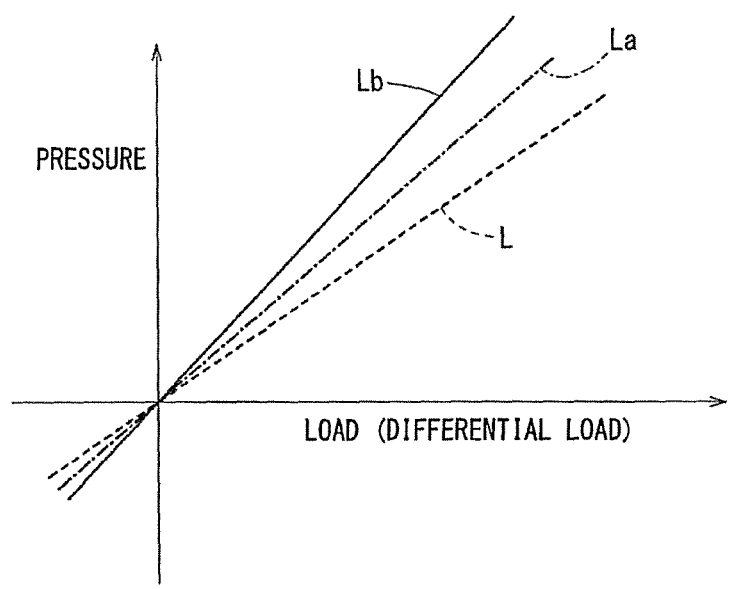
FIG. 11B is an explanatory diagram of correction of a calibration curve.

In addition, in a second calibration curve correction step of step S10, the second calibration curve correction unit 124 corrects the slope of the calibration curve La on the basis of the temperature acquired in the second temperature acquisition step (see FIG. 11B). Consequently, a calibration curve Lb, the slope of which has been corrected, is obtained.

Further, in a second reaction force correction step of step S11, the second reaction force correction unit 122 corrects the reaction force detected in the reaction force detecting step on the basis of the temperature acquired in the second temperature acquisition step. Consequently, using the reaction force of the third applied load measurement unit 66, it is possible to accurately calculate in real time the reaction force of the first applied load measurement unit 56, which changes depending on the temperature and the time period during which the blood components are collected.

Thereafter, in the internal pressure calculation step of step S12, the internal pressure (circuit internal pressure) of the first applied load measurement unit 56 is calculated on the basis of the calibration curve Lb, and a differential load which is obtained by subtracting the reaction force of the first applied load measurement unit 56 obtained in the second reaction force correcting step from the load detected by the first load detecting unit 88.

In this case, the blood component collection system 10A and the circuit internal pressure acquisition method according to the present embodiment exhibit the following effects.

Figure 12A:
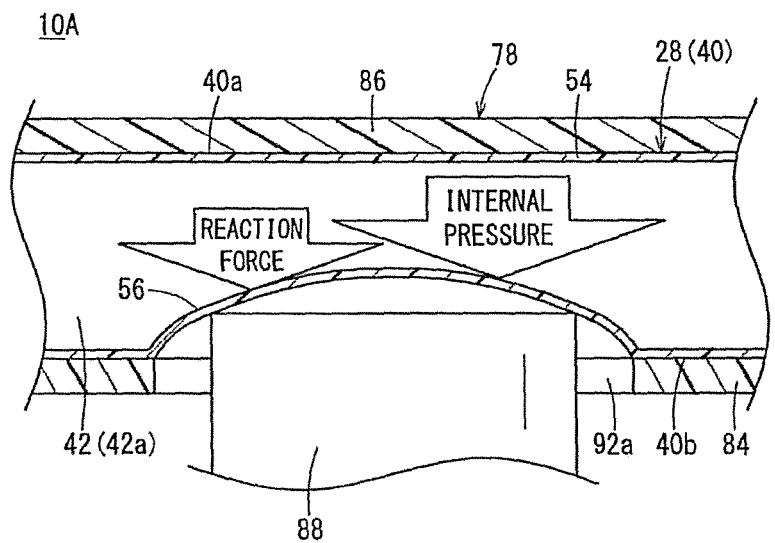
FIG. 12A is a view for explaining the detection of loads at a positive pressure.
Figure 12B:
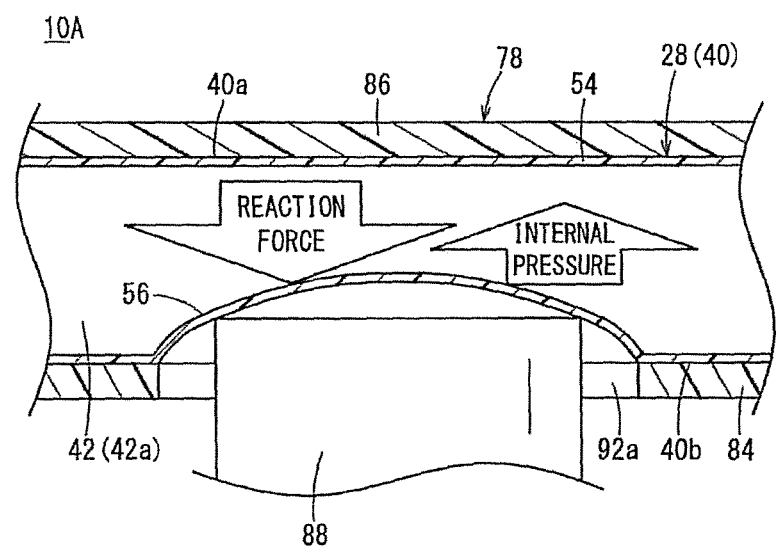
FIG. 12B is a view for explaining the detection of loads at a negative pressure.

In the case that the collection and returning pump 100 is in operation during blood component collection (during a blood collection operation or during a blood returning operation), then by the first load detecting unit 88, a load is detected which is the sum of the internal pressure (circuit internal pressure) of the blood collection line 42a through which the blood flows, and the reaction force of the first applied load measurement unit 56 (a restorative force accompanying deformation of the first applied load measurement unit 56). That is, in the case that the circuit internal pressure is a positive pressure, as shown in FIG. 12A, the load detected by the first load detecting unit 88 (the pressing force from the first applied load measurement unit 56) is obtained simply by adding the circuit internal pressure and the reaction force. On the other hand, in the case that the circuit internal pressure is a negative pressure, as shown in FIG. 12B, the load detected by the first load detecting unit 88 is obtained simply by subtracting the absolute value of the circuit internal pressure from the reaction force.

Figure 13:
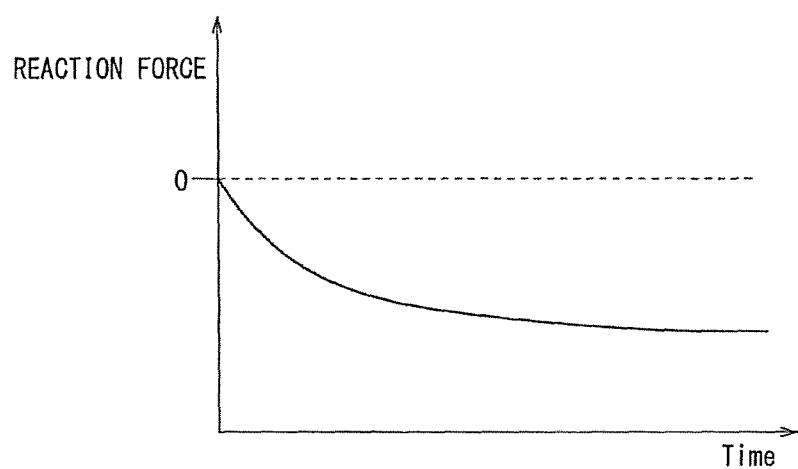
FIG. 13 is a diagram for explaining a decrease in a reaction force occurring over time.

However, as shown in FIG. 13, the reaction force of the first applied load measurement unit 56 decreases over time. In FIG. 13, an image is shown of a temporal change in the reaction force of the first applied load measurement unit 56 in the case that the reaction force of the first applied load measurement unit 56 when the cassette 28 is mounted in the cassette mounting unit 78 is set to zero. The reason that the reaction force of the first applied load measurement unit 56 decreases over time in the foregoing manner is due to the fact that creep is generated accompanying continuation of a state in which the first applied load measurement unit 56 is pressed by the first load detecting unit 88. Accordingly, when a fixed value that does not change over time is used as the reaction force of the first applied load measurement unit 56, the measurement accuracy of the circuit internal pressure is lowered.

Thus, in the blood component collection system 10A, the reaction force of the third applied load measurement unit 66, which decreases over time in the same manner as the reaction force of the first applied load measurement unit 56, is detected in real time and used to calculate the circuit internal pressure. Moreover, since the hollow portion 43 is closed in a state of normal pressure, the internal pressure of the hollow portion 43 is always 0 mmHg. Therefore, the load detected by the third load detecting unit 90 is only the reaction force of the third applied load measurement unit 66 (the restorative force accompanying deformation of the third applied load measurement unit 66).

Further, when introduction of blood is started, since the blood flows through the blood collection line 42a, whereas the blood does not flow through the hollow portion 43, the temperature of the first applied load measurement unit 56 becomes higher than the temperature of the third applied load measurement unit 66. When this happens, since the reaction force of the first applied load measurement unit 56 changes due to temperature, in a state in which blood is made to flow through the blood collection line 42a, the reaction force of the third applied load measurement unit 66 as detected by the third load detecting unit 90 does not become the same as the reaction force of the first applied load measurement unit 56. Furthermore, the calibration curve La of the first applied load measurement unit 56 changes in accordance with the temperature change of the first applied load measurement unit 56 accompanying the introduction of blood therein. Stated otherwise, the internal pressure calculation data changes in accordance with the change in temperature.

Therefore, when calculating the internal pressure of the first applied load measurement unit 56, the internal pressure calculation unit 116 carries out a calculation that reflects a change in the internal pressure calculation data due to temperature. Consequently, the internal pressure (circuit internal pressure) of the first applied load measurement unit 56 can be accurately measured. The circuit internal pressure, for example, ranges from −300 mmHg to 500 mmHg.

The internal pressure calculation data is data including the reaction force of the applied load measurement unit (first applied load measurement unit 56). The internal pressure calculation unit 116 carries out a calculation that reflects a change in the reaction force of the applied load measurement unit (first applied load measurement unit 56) due to temperature. Further, in the internal pressure calculation step, a calculation is performed in which there is reflected the change in the reaction force of the applied load measurement unit (first applied load measurement unit 56) due to temperature. Consequently, the internal pressure of the applied load measurement unit (first applied load measurement unit 56) can be measured more accurately.

The separation device (centrifugal separation device 14) is equipped with the information acquisition unit (temperature acquisition unit 106) that acquires influence information (temperature) that exerts an influence on the reaction force of the applied load measurement unit (first applied load measurement unit 56), and the internal pressure calculation unit 116 performs a calculation reflecting the change in the reaction force of the applied load measurement unit (first applied load measurement unit 56) due to temperature, on the basis of the influence information acquired by the information acquisition unit (temperature acquisition unit 106).

In the circuit internal pressure acquisition method, the information acquisition step (second temperature acquisition step) is performed in which influence information (temperature) is acquired that exerts an influence on the reaction force of the applied load measurement unit (first applied load measurement unit 56), and in the internal pressure calculation step, a calculation is performed reflecting the change in the reaction force of the applied load measurement unit (first applied load measurement unit 56) due to temperature, on the basis of the influence information (temperature) acquired in the information acquisition step (second temperature acquisition step).

Consequently, when calculating the internal pressure of the first applied load measurement unit 56, a calculation can easily be carried out that reflects a change in the reaction force of the first applied load measurement unit 56 due to temperature.

The biological component collection device (cassette 28) includes the hollow portion forming member 53 made of a soft material, and which forms the hollow portion 43 through which the biological liquid (blood) and the biological components (blood components) do not flow during operation of the separation device (centrifugal separation device 14). The separation device (centrifugal separation device 14) is equipped with the reaction force detecting unit (third load detecting unit 90) that detects the reaction force of the applied reaction force measurement unit (third applied load measurement unit 66) that makes up a portion of the hollow portion forming member 53, in order to obtain the reaction force of the applied load measurement unit (first applied load measurement unit 56) which changes in accordance with the time period during collection of the biological components (during collection of the blood components) in the device attached state (cassette attached state), and the reaction force correction unit (second reaction force correction unit 122) that corrects the reaction force detected by the reaction force detecting unit (third load detecting unit 90) using the influence information (temperature) acquired by the information acquisition unit (temperature acquisition unit 106). The internal pressure calculation unit 116 calculates the internal pressure of the applied load measurement unit (first applied load measurement unit 56) using the reaction force corrected by the reaction force correction unit (second reaction force correction unit 122).

Further, in the circuit internal pressure acquisition method, there are preformed the reaction force detecting step of detecting the reaction force of the applied reaction force measurement unit (third applied load measurement unit 66) that makes up a portion of the hollow portion forming member 53, in order to acquire the reaction force of the applied load measurement unit (first applied load measurement unit 56) which changes in accordance with the time period during collection of the biological components (during collection of the blood components) in the device attached state (cassette attached state), and the reaction force correction step of correcting the reaction force detected in the reaction force detecting step using the influence information (temperature) acquired in the information acquisition step (second temperature acquisition step). In the internal pressure calculation step, the internal pressure of the applied load measurement unit (first applied load measurement unit 56) is calculated using the reaction force corrected in the reaction force correction step.

Consequently, the reaction force detected by the reaction force detecting unit (third load detecting unit 90) is corrected on the basis of the influence information (temperature of the line forming member 52) acquired by the information acquisition unit (temperature acquisition unit 106), and since the internal pressure of the applied load measurement unit (first applied load measurement unit 56) is calculated using such a corrected reaction force, it is possible to accurately measure the circuit internal pressure.

The load detecting unit (first load detecting unit 88) presses on the applied load measurement unit (first applied load measurement unit 56) in the device attached state (cassette attached state). Owing to this feature, the circuit internal pressure can be accurately measured with a simple configuration.

The influence information acquired by the information acquisition unit (temperature acquisition unit 106) is the temperature of the line forming member 52. In accordance with this feature, it is possible to accurately correct the reaction force of the applied load measurement unit (first applied load measurement unit 56).

The internal pressure calculation data is data including the calibration curve La indicative of a relationship between a differential load obtained by subtracting the reaction force of the applied load measurement unit (first applied load measurement unit 56) from the load detected by the load detecting unit (first load detecting unit 88), and the internal pressure of the applied load measurement unit (first applied load measurement unit 56), and the internal pressure calculation unit 116 performs a calculation reflecting a change in the calibration curve La due to temperature. Consequently, the internal pressure (circuit internal pressure) of the applied load measurement unit (first applied load measurement unit 56) can be measured more accurately.

The separation device (centrifugal separation device 14) is equipped with the load detecting unit for calibration (second load detecting unit 89) that detects the load applied to the applied load measurement unit for calibration (second applied load measurement unit 60) that constitutes part of the line forming member 52 in the device attached state (cassette attached state), the internal pressure calculation unit for calibration 112 that calculates the internal pressure of the applied load measurement unit for calibration (second applied load measurement unit 60) using the load detected by the load detecting unit for calibration (second load detecting unit 89) and the internal pressure calculation data for calibration, before collection of the biological components (collection of the blood components) is performed in the device attached state (cassette attached state), and the correction unit (first correction unit 108) that corrects the internal pressure calculation data using the internal pressure calculated by the internal pressure calculation unit for calibration 112. The internal pressure calculation data for calibration is data indicative of a relationship between the load detected by the load detecting unit for calibration (second load detecting unit 89) and the internal pressure of the applied load measurement unit for calibration (second applied load measurement unit 60), and the internal pressure calculation unit for calibration 112 performs a calculation reflecting a change in the internal pressure calculation data for calibration due to temperature. Consequently, the internal pressure of the applied load measurement unit for calibration (second applied load measurement unit 60) can be accurately measured.

The biological component collection device (blood component collection cassette 28) includes the line forming member 52, which is made of a soft material, and forms the biological liquid line (blood line 42) through which the biological liquid (blood) or the biological components (blood components) flow, and the temperature measured section 59 in which the temperature on the line forming member 52 is measured. The separation device (centrifugal separation device 14) is equipped with the load detecting unit (first load detecting unit 88) that detects the load applied to the applied load measurement unit (first applied load measurement unit 56) which partially makes up the line forming member 52 in the device attached state (cassette attached state) in which the biological component collection device (blood component collection cassette 28) is attached to the separation device (centrifugal separation device 14), the temperature acquisition unit 106 that acquires the temperature of the temperature measured section 59, the correction unit (second correction unit 110) that corrects the internal pressure calculation data indicative of a relationship between the load detected by the load detecting unit (first load detecting unit 88) and the internal pressure of the applied load measurement unit (first applied load measurement unit 56) on the basis of the temperature acquired by the temperature acquisition unit 106, and the internal pressure calculation unit 116 that calculates the internal pressure of the applied load measurement unit (first applied load measurement unit 56) using the load detected by the load detecting unit (first load detecting unit 88) and the internal pressure calculation data that was corrected by the correction unit (second correction unit 110), during collection of the biological components (collection of blood components) in which the biological liquid (blood) or the biological components (blood components) are made to flow through the biological liquid line (blood line 42) in the device attached state (cassette attached state). Consequently, it is possible to accurately measure the internal pressure (circuit internal pressure) of the applied load measurement unit (first applied load measurement unit 56).

Figure 14:
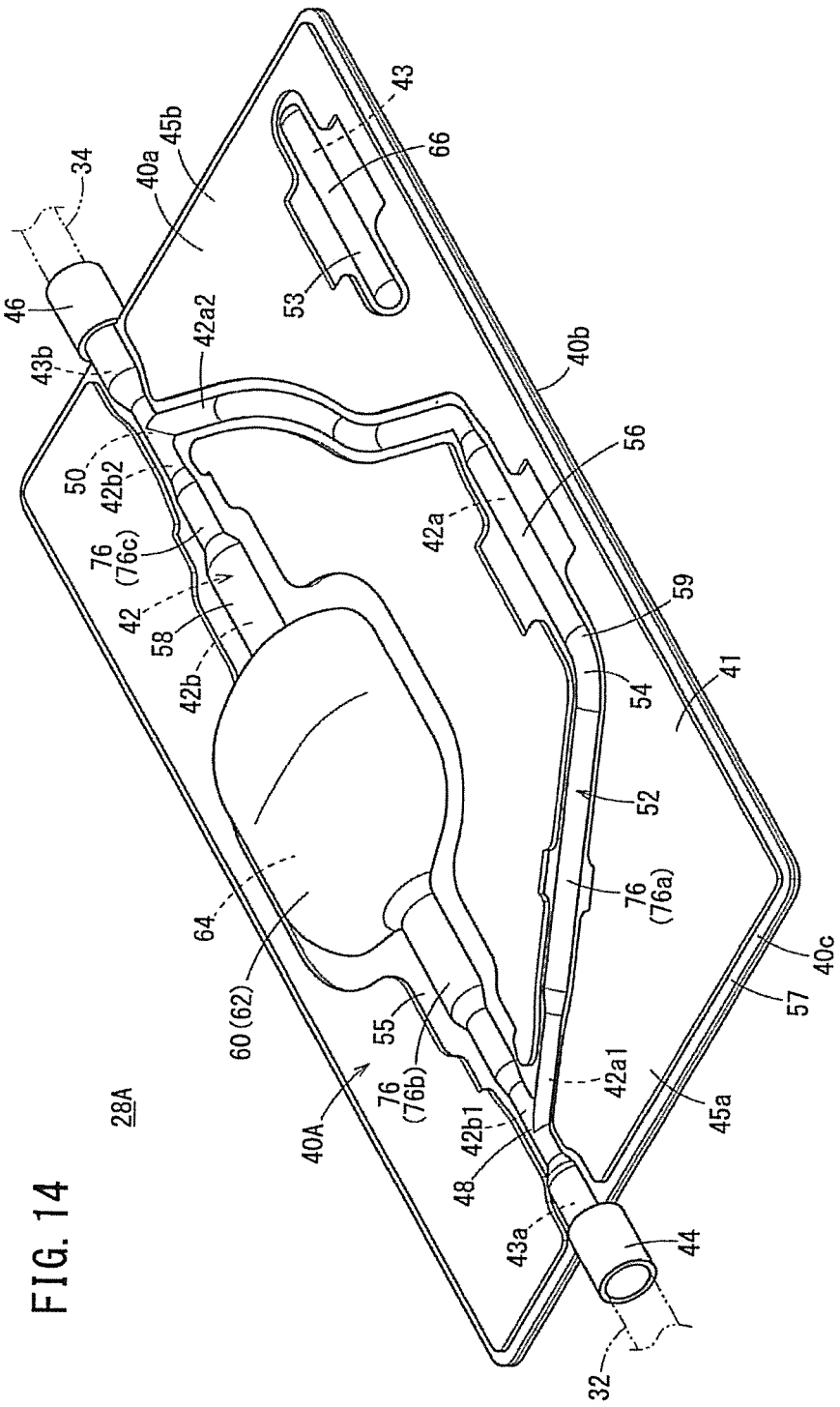
FIG. 14 is a perspective view of a cassette according to a modified example.

In the above-described blood component collection system 10A, the blood component collection cassette 28A (hereinafter referred to as a "cassette 28A") shown in FIG. 14 may be adopted instead of the cassette 28. In the cassette body 40A of the cassette 28A, the hollow portion 43 is a flow path which is independent of the blood collection line 42a and is not in fluid communication therewith. Accordingly, the hollow portion 43 is a space that is independent of the blood collection line 42a at all times, and air is enclosed in the interior thereof. The configuration of other parts of the cassette 28A is the same as that of the cassette 28 shown in FIG. 2, etc. In accordance with the cassette 28A, the clamp 72d (see FIG. 4) in the centrifugal separation device 14 can be rendered unnecessary. Therefore, the configuration of the centrifugal separation device 14 can be simplified, together with simplifying the controls related to operation of the clamps 72.

Second Embodiment

Next, a blood component collection system 10B, which is a second embodiment of the biological component collection system according to the present invention, will be described. In the blood component collection system 10B according to the second embodiment, the same reference numerals are assigned to constituent elements which are the same as the constituent elements described in the above-described first embodiment, and detailed description of such features will be omitted. In the second embodiment, concerning configurations thereof which are the same as those of the aforementioned first embodiment, the same functions and effects are exhibited.

Figure 15:
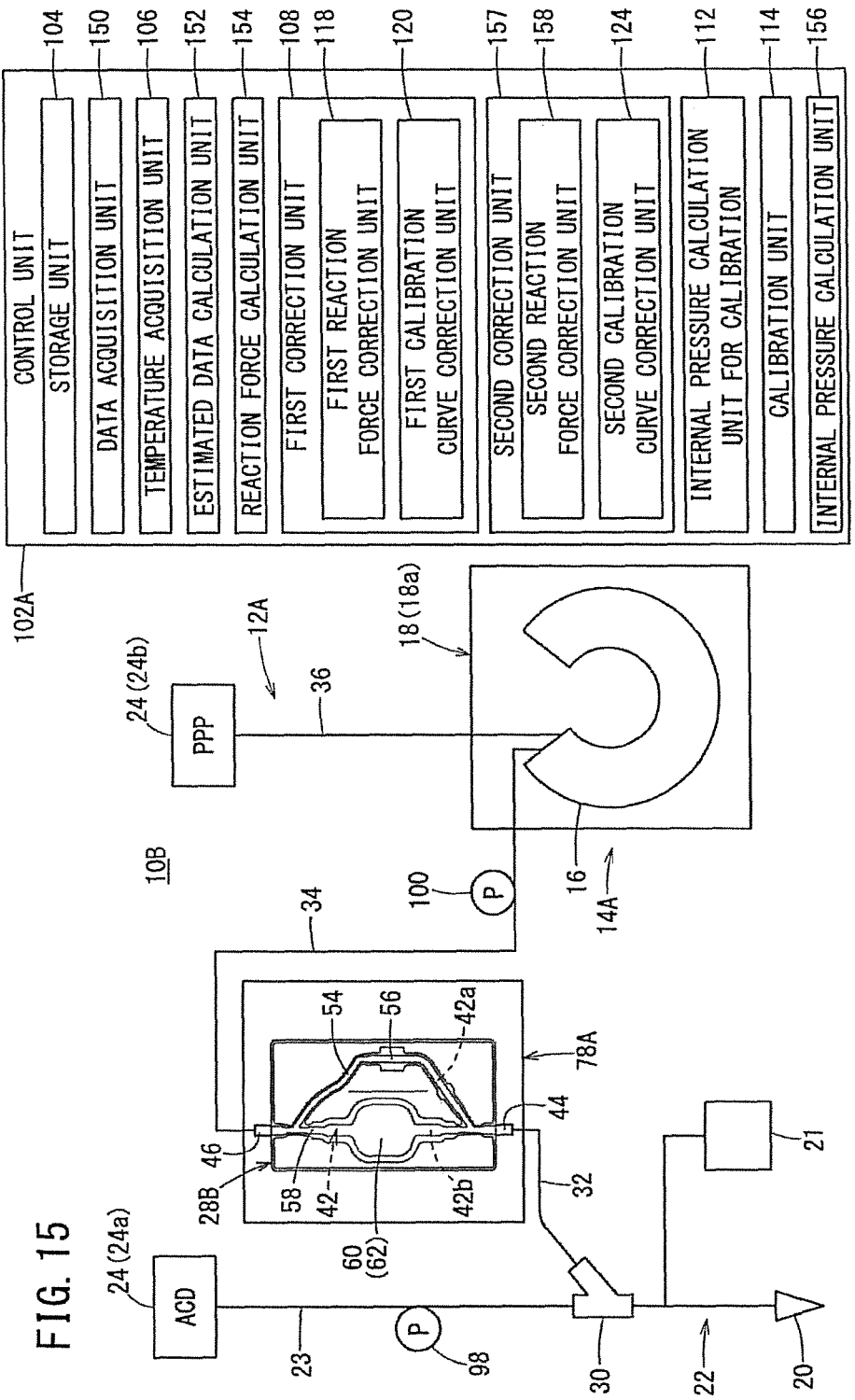
FIG. 15 is a schematic diagram of a blood component collection system according to a second embodiment of the present invention.
Figure 16:
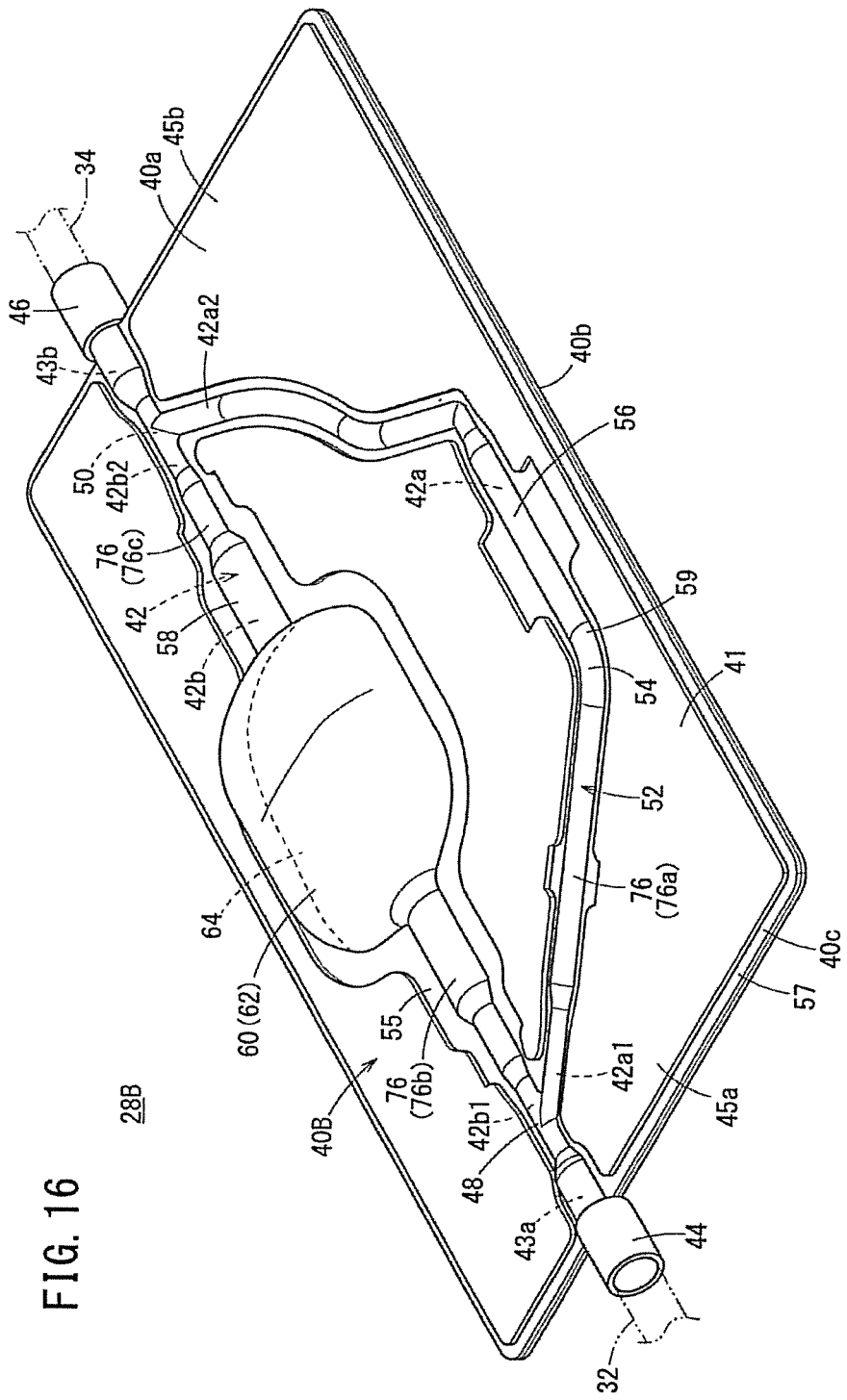
FIG. 16 is a perspective view of a blood component collection cassette shown in FIG. 15.

As shown in FIG. 15, the blood component collection system 10B comprises a blood collection circuit set 12A and a centrifugal separation device 14A. The blood collection circuit set 12A includes a blood component collection cassette 28B (hereinafter referred to as a "cassette 28B"). Configurations of the blood collection circuit set 12A other than the cassette 28B are the same as those in the above-described blood collection circuit set 12. As shown in FIG. 16, a cassette body 40B of the cassette 28B does not include the aforementioned hollow portion 43 (see FIG. 2) and the clamp action member 76d (see FIG. 2). Other portions of the cassette 28B are configured in the same manner as in the configuration of the cassette 28 shown in FIG. 2, etc.

Figure 17:
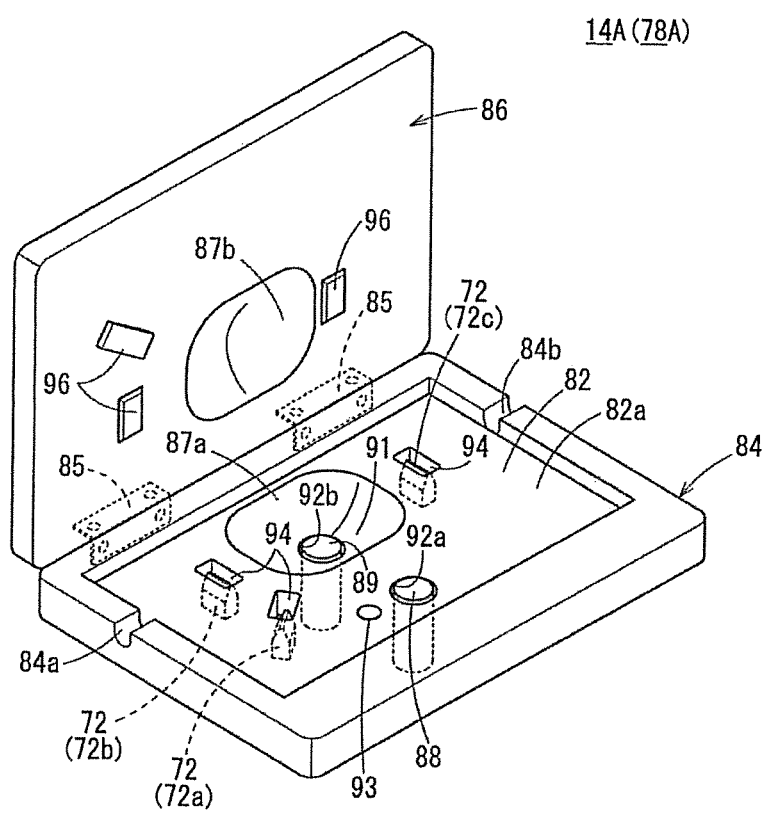
FIG. 17 is a perspective view of a cassette mounting unit shown in FIG. 15.

As shown in FIG. 15, the centrifugal separation device 14A includes a centrifuge unit 18, a cassette mounting unit 78A, and a control unit 102A. In FIG. 17, in the cassette mounting unit 78A, the third load detecting unit 90, the third through hole 92c, the clamp 72d, the hole 94 in which the clamp 72d is inserted, and the projection 96 corresponding to the clamp 72d shown in FIG. 3, etc., are not provided. The configuration of other parts of the cassette mounting unit 78A is the same as that of the cassette mounting unit 78 shown in FIG. 3, etc.

In FIG. 15, the control unit 102A is a computation device including a microcomputer, and has a CPU (central processing unit), and a ROM, a RAM, etc., serving as memories, wherein by reading out and executing programs stored in the ROM, the CPU functions as various function realizing units (function realizing means). Moreover, the various function realizing units may be constituted by function realizing devices in the form of hardware.

The control unit 102A comprises a storage unit 104, a data acquisition unit 150, a temperature acquisition unit 106 (information acquisition unit), a first correction unit 108, a second correction unit 157, an internal pressure calculation unit for calibration 112, a calibration unit 114, an estimated data calculation unit 152, a reaction force calculation unit 154, and an internal pressure calculation unit 156.

Before collection of blood components during which blood or blood components are made to flow in the blood line 42 in the cassette attached state, using the load detected by the first load detecting unit 88, the data acquisition unit 150 acquires initial data A (see FIG. 19) indicative of a temporal change in the reaction force of the first applied load measurement unit 56.

On the basis of the initial data A, the estimated data calculation unit 152 calculates estimated data B (see FIG. 19) for the purpose of estimating the reaction force of the first applied load measurement unit 56 which changes depending on the time period during collection of the blood components and the temperature of the first applied load measurement unit 56. More specifically, the estimated data calculation unit 152 calculates the estimated data B using a least squares method based on the initial data A.

During collection of the blood components, the reaction force calculation unit 154 calculates the reaction force of the first applied load measurement unit 56 based on the estimated data B. The second correction unit 157 corrects the internal pressure calculation data based on the temperature acquired by the temperature acquisition unit 106. The second correction unit 157 includes a second reaction force correction unit 158 and a second calibration curve correction unit 124. On the basis of the temperature acquired by the temperature acquisition unit 106, the second reaction force correction unit 158 corrects the reaction force of the first applied load measurement unit 56 calculated by the reaction force calculation unit 154.

In the cassette attached state, during collection of the blood components, the internal pressure calculation unit 156 calculates the internal pressure (circuit internal pressure) of the first applied load measurement unit 56, using the load detected by the first load detecting unit 88, and the internal pressure calculation data which is corrected by the second correction unit 157. Stated otherwise, the internal pressure calculation unit 156 carries out a calculation that reflects a change in the internal pressure calculation data due to temperature.

Next, a circuit internal pressure acquisition method in which the blood component collection system 10B is used will be described with reference to the flowchart shown in FIG. 18.

Figure 18:
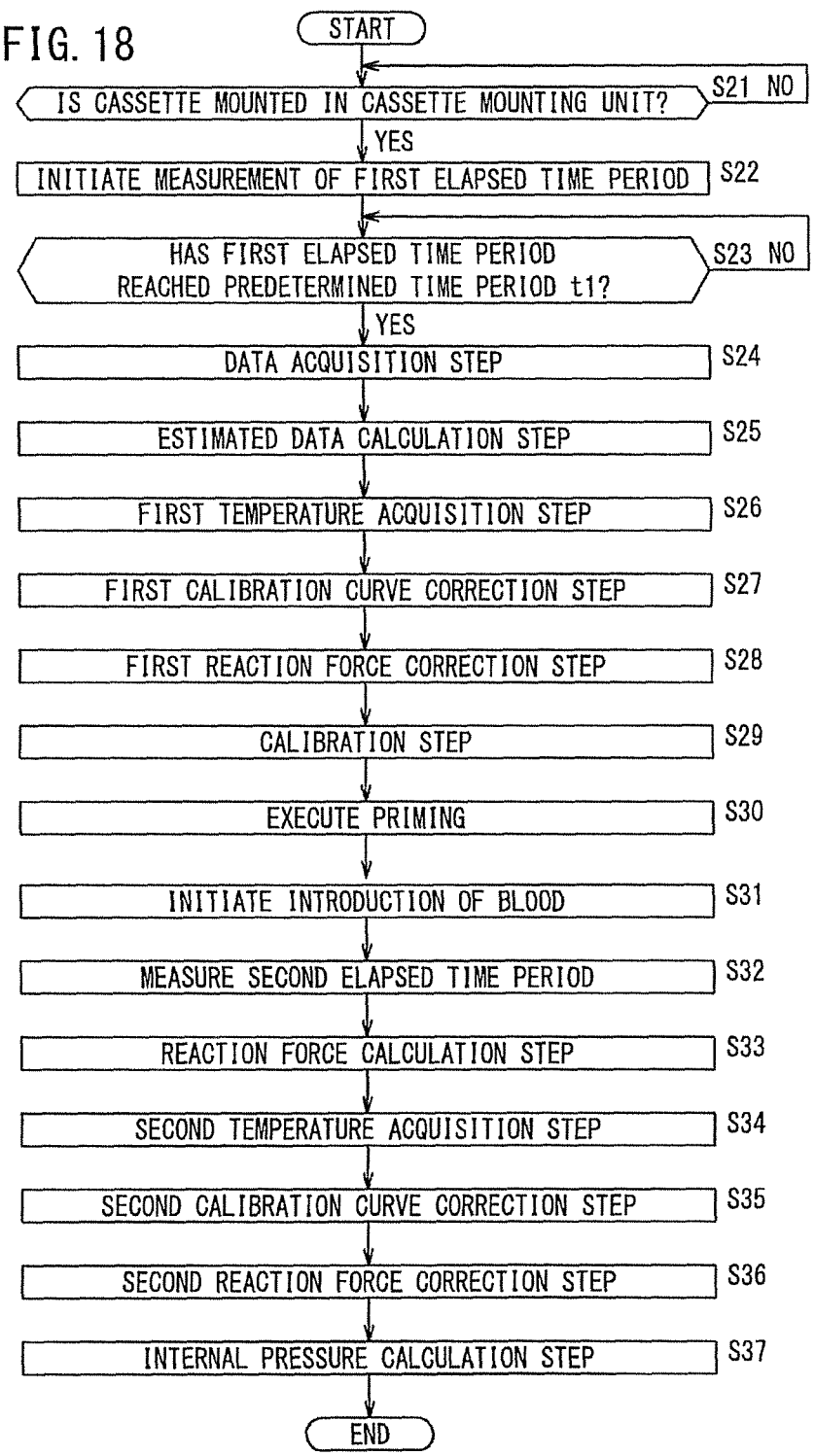
FIG. 18 is a flowchart for describing a circuit internal pressure acquisition method according to the second embodiment of the present invention.

As shown in FIG. 18, in step S21, the control unit 102A determines whether or not the cassette 28B has been mounted in the cassette mounting unit 78A. More specifically, the control unit 102A determines that the cassette 28B has been mounted in the cassette mounting unit 78A when the lid 86 is closed, in a state in which the cassette 28B is mounted in the cassette mounting groove 82 of the attachment base 84.

If the control unit 102A determines that the cassette 28B is not mounted in the cassette mounting unit 78A (step S21: NO), the process remains at step S21 until it is determined that the cassette 28B has been mounted in the cassette mounting unit 78A.

In the case it is determined by the control unit 102A that the cassette 28B has been mounted in the cassette mounting unit 78A (step S21: YES), then in step S22, the control unit 102A initiates measurement of a first elapsed time period from when the control unit 102A determines that the cassette 28B has been mounted in the cassette mounting unit 78A. Subsequently, in step S23, the control unit 102A determines whether or not the first elapsed time period has reached the predetermined time period t1 (see FIG. 19). In this instance, although the predetermined time period t1 can be arbitrarily set, the predetermined time period t1 may be set to five minutes, for example.

If the control unit 102A determines that the first elapsed time period has not reached the predetermined time period t1 (step S23: NO), the process remains at step S23 until it is determined that the first elapsed time period has reached the predetermined time period t1. In the case it is determined by the control unit 102A that the first elapsed time period has reached the predetermined time period t1 (step S23: YES), then in step S24, a data acquisition step is performed.

Figure 19:
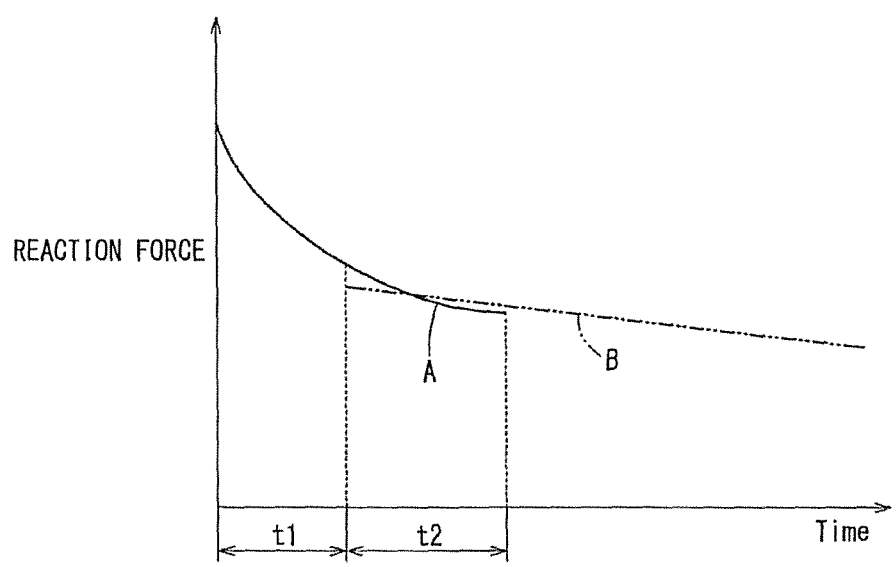
FIG. 19 is a graph for describing estimated data.

As shown in FIG. 19, in the data acquisition step, before collection of blood components is performed, the data acquisition unit 150, using the load detected by the first load detecting unit 88 during a predetermined data acquisition time period t2, acquires the initial data A indicative of the temporal change in the reaction force of the first applied load measurement unit 56. In this instance, although the predetermined time period t2 can be arbitrarily set, the predetermined time period t2 may be set to five minutes, for example.

As shown in FIG. 19, in the estimated data calculation step of step S25 of FIG. 18, on the basis of the initial data A, the estimated data calculation unit 152 calculates estimated data B (a baseline) for the purpose of estimating the reaction force of the first load detecting unit 88 that changes depending on the time period during which the blood components are collected. More specifically, in the estimated data calculation step, the estimated data calculation unit 152 calculates the estimated data B using the results obtained using a least squares method based on the initial data A, and a correction variable that is a function of temperature. The correction variable can be acquired in advance by experiment or analysis. Consequently, it is possible to accurately calculate the reaction force of the first applied load measurement unit 56 in real time, which changes depending on the time period during which the blood components are collected. The calculated estimated data B is saved (stored) in the storage unit 104.

Next, a first temperature acquisition step (step S26), a first calibration curve correction step (step S27), a first reaction force correction step (step S28), and a calibration step (step S29) are performed. The processes from step S26 to step S29 are the same as the above-described processes from step S1 to step S4 of FIG. 10.

Subsequently, in step S30 of FIG. 18, the ACD solution transfer pump 98 is driven, and carries out the aforementioned priming in which the ACD solution is filled until immediately before the blood line 42 of the cassette 28B. Thereafter, in step S31, blood is introduced into the blood line 42 of the cassette 28B. At this time, in step S32, the control unit 102A starts to measure a second elapsed time period from the start of flow of blood in the blood collection line 42a.

Next, in the reaction force calculation step of step S33, during collection of the blood components, the reaction force calculation unit 154 calculates the reaction force of the first applied load measurement unit 56 on the basis of the second elapsed time period and the estimated data B.

Subsequently, in the second temperature acquisition step of step S34, the temperature acquisition unit 106 calculates the temperature (temperature of the wall portion of the blood line 42) of the line forming member 52 on the basis of the second elapsed time period and the time and temperature curve (temperature calculation data). More specifically, the process of the second temperature acquisition step (information acquisition step) is the same as the process of the aforementioned second temperature acquisition step of step S9 of FIG. 10.

In addition, the second calibration curve correction step of step S35 is performed. The process of step S35 is the same as the above-described process of step S10 of FIG. 10.

Further, in the second reaction force correction step of step S36, the second reaction force correction unit 158 corrects the reaction force detected in the reaction force calculation step on the basis of the temperature acquired in the second temperature acquisition step. Consequently, it is possible to accurately calculate the reaction force of the first applied load measurement unit 56 in real time, which changes depending on the time period during which the blood components are collected and the temperature.

Thereafter, in the internal pressure calculation step of step S37, during collection of the blood components, the internal pressure calculation unit 156 calculates the internal pressure (circuit internal pressure) of the first applied load measurement unit 56 on the basis of the calibration curve Lb and the differential load, which is obtained by subtracting the reaction force obtained in the second reaction force correction step from the load detected by the first load detecting unit 88.

In the present invention, the separation device (centrifugal separation device 14A) includes the data acquisition unit 150 that acquires the initial data indicative of a temporal change in the reaction force of the applied load measurement unit (first applied load measurement unit 56) using the load detected by the load detecting unit (first load detecting unit 88) before collection of the biological components (collection of the blood components) is performed in the device attached state (cassette attached state), the estimated data calculation unit 152 that calculates, on the basis of the initial data A, the estimated data for predicting the reaction force of the applied load measurement unit (first applied load measurement unit 56) which changes in accordance with the time period during collection of the biological components (during collection of the blood components), the reaction force calculation unit 154 that calculates the reaction force of the applied load measurement unit (first applied load measurement unit 56) using the estimated data B during collection of the biological components (during collection of the blood components), and the reaction force correction unit (second reaction force correction unit 158) which corrects the reaction force calculated by the reaction force calculation unit 154 using the influence information (temperature) acquired by the information acquisition unit (temperature acquisition unit 106). The internal pressure calculation unit 156 calculates the internal pressure of the applied load measurement unit (first applied load measurement unit 56) using the reaction force corrected by the reaction force correction unit (second reaction force correction unit 158).

Further, in the circuit internal pressure acquisition method, there are performed the data acquisition step of acquiring initial data A indicative of a temporal change in the reaction force of the applied load measurement unit (first applied load measurement unit 56) using the load detected by the load detecting step before collection of the biological components (collection of the blood components) is performed in the device attached state (cassette attached state), the estimated data calculation step of calculating, on the basis of the initial data A, estimated data for predicting the reaction force of the applied load measurement unit (first applied load measurement unit 56) which changes in accordance with the time period during collection of the biological components (during collection of the blood components), the reaction force calculation step of calculating the reaction force of the applied load measurement unit (first applied load measurement unit 56) using the estimated data B during collection of the biological components (during collection of the blood components), and the reaction force correction step (second reaction force correction step) of correcting the reaction force calculated in the reaction force calculation step using the influence information (temperature) acquired in the information acquisition step (second temperature acquisition step). In the internal pressure calculation step, the internal pressure of the applied load measurement unit (first applied load measurement unit 56) is calculated using the reaction force corrected in the reaction force correction step (second reaction force correction step).

In accordance with these features, it is possible to accurately calculate the reaction force of the applied load measurement unit (first applied load measurement unit 56) that changes depending on the time period and the temperature. Accordingly, the circuit internal pressure can be accurately measured.

The estimated data calculation unit 152 calculates the estimated data B using a least squares method based on the initial data A. Consequently, it is possible to easily calculate the estimated data B.

The biological component collection device is not limited to being in the form of the cassette 28, 28A, or 28B. Accordingly, the biological component collection device may be equipped with a first soft tube member having the blood collection line 42a, and a second soft tube member having the blood returning line 42b, and may be constituted in a manner so that both end portions of the first soft tube member and the second soft tube member are connected together respectively via connectors.

The internal pressure calculation data that is used when calculating the circuit internal pressure using the load detected by the first load detecting unit 88 is not limited to the calibration curve L, but may be a table that is prepared beforehand. The first load detecting unit 88, the second load detecting unit 89, and the third load detecting unit 90 may be configured in a manner so as to measure the load (in a non-contact manner) without applying pressure to the first applied load measurement unit 56, the second applied load measurement unit 60, and the third applied load measurement unit 66.

The influence information that is acquired by the information acquisition unit is not limited to the temperature of the line forming member 52, but may be an elapsed time period from flowing of the biological liquid through the biological liquid line (blood line 42) or a hardness of the line forming member 52 (first applied load measurement unit 56).

The scope of application of the present invention is not limited to a blood component collection system 10A, 10B, but may be applied to various systems through which a liquid is made to flow through a flow path, for example, a whole blood donation system, or a culture apparatus for various types of cells which are collected or cultured from patients or donors, or alternatively, a medicinal solution administration system, or the like. Accordingly, the liquid that flows in the biological component collection device (biological component collection system) is not limited to blood.

The biological component collection system and the circuit internal pressure acquisition method according to the present invention are not limited to the above-described embodiments, and it goes without saying that various modifications could be adopted therein within a range that does not depart from the essence and gist of the present invention.

DESCRIPTION OF REFERENCE CHARACTERS

10A, 10B . . . blood component collection system (biological component collection system)
14, 14A . . . centrifugal separation device (separation device)
28, 28A, 28B . . . blood component collection cassette (biological component collection device)
42 . . . blood line (biological liquid line)
56 . . . first applied load measurement unit (applied load measurement unit)
60 . . . second applied load measurement unit
66 . . . third applied load measurement unit
88 . . . first load detecting unit (load detecting unit)
89 . . . second load detecting unit
90 . . . third load detecting unit (reaction force detecting unit)
106 . . . temperature acquisition unit (information acquisition unit)
116, 156 . . . internal pressure calculation unit
118 . . . first reaction force correction unit
122, 158 . . . second reaction force correction unit

The invention claimed is:

1. A biological component collection system equipped with a separation device adapted to separate a biological component from a biological liquid, and a biological component collection device configured to be attachable to the separation device and collect a desired biological component from the biological liquid;
   wherein the biological component collection device includes a line forming member comprised of a deformable polymer comprised of vinyl chloride, polyolefin, or polyurethane, and forming a biological liquid line through which the biological liquid or the biological component flows; and
   an applied load measurement unit which partially makes up the line forming member;
   the separation device comprising:
   a load detecting unit adapted to detect a load applied to said applied load measurement unit in a device attached state in which the biological component collection device is attached to the separation device;
   a temperature measurement unit for detecting of a detected temperature of the line forming member of the biological component collection device, and
   an internal pressure calculation unit adapted to calculate an internal pressure of the applied load measurement unit, using the load detected by the load detecting unit and internal pressure calculation data, during collection of the biological component in which the biological liquid or the biological component is made to flow through the biological liquid line in the device attached state;
   wherein the internal pressure calculation data is data indicative of a relationship between the load detected by the load detecting unit and the internal pressure of the applied load measurement unit; and
   when calculating the internal pressure of the applied load measurement unit, the internal pressure calculation unit performs a calculation reflecting a change in the internal pressure calculation data depending on said detected temperature
   wherein:
   said biological component collection device further comprises a hollow portion forming member and
   said separation device further comprises a reaction force measurement unit for measuring a reaction force of the hollow portion forming member, and
   the internal pressure calculation data is data including measurements of said reaction force of the hollow portion forming member; and
   the internal pressure calculation unit performs a correction reflecting a change in the reaction force of the hollow portion forming member and said detected temperature of the line forming member.

2. The biological component collection system according to claim 1, wherein:
the separation device comprises an information acquisition unit adapted to acquire influence information that exerts an influence on the reaction force of the applied load measurement unit; and
the internal pressure calculation unit performs a calculation reflecting the change in the reaction force of the applied load measurement unit due to temperature, on a basis of the influence information acquired by the information acquisition unit.

3. The biological component collection system according to claim 2, wherein:
said hollow portion forming member is comprised of a deformable polymer comprised of vinyl chloride, polyolefin, or polyurethane, and which forms a hollow portion through which the biological liquid and the biological component do not flow during operation of the separation device; and
said separation unit further comprises a reaction force detecting unit adapted to detect a reaction force in a portion of the hollow portion forming member, in order to obtain an internal pressure of the applied load measurement unit which changes in accordance with a time period during collection of the biological component in the device attached state; and
a reaction force correction unit adapted to correct the reaction force detected by the reaction force detecting unit using the influence information acquired by the information acquisition unit;
wherein the internal pressure calculation unit calculates the internal pressure of the applied load measurement unit using the reaction force corrected by the reaction force correction unit.

4. The biological component collection system according to claim 2, wherein the separation device comprises:
a data acquisition unit adapted to acquire initial data indicative of a temporal change in the reaction force of the applied load measurement unit using the load detected by the load detecting unit, in the device attached state before collection of the biological component;
an estimated data calculation unit adapted to calculate, on a basis of the initial data, estimated data for predicting the reaction force of the applied load measurement unit which changes in accordance with the time period during collection of the biological component;
a reaction force calculation unit adapted to calculate the reaction force of the applied load measurement unit using the estimated data during collection of the biological component; and
a reaction force correction unit adapted to correct the reaction force calculated by the reaction force calculation unit using the influence information acquired by the information acquisition unit;
wherein the internal pressure calculation unit calculates the internal pressure of the applied load measurement unit using the reaction force corrected by the reaction force correction unit.

5. The biological component collection system according to claim 4, wherein the estimated data calculation unit calculates the estimated data using a least squares method based on the initial data.

6. The biological component collection system according to claim 5, wherein the influence information acquired by the information acquisition unit is an elapsed time from flowing of the biological liquid in the biological liquid line, a temperature of the line forming member, or a hardness of the line forming member.

7. The biological component collection system according to claim 6, wherein the load detecting unit presses on the applied load measurement unit in the device attached state.

8. The biological component collection system according to claim 7, wherein:
the internal pressure calculation data is data including a calibration curve indicative of a relationship between a differential load obtained by subtracting the reaction force of the applied load measurement unit from the load detected by the load detecting unit, and the internal pressure of the applied load measurement unit; and
the internal pressure calculation unit performs a calculation reflecting a change in the calibration curve due to temperature.

9. The biological component collection system according to claim 8, wherein the separation device comprises:
a load detecting unit for calibration adapted to detect a load applied to an applied load measurement unit for calibration that constitutes part of the line forming member in the device attached state;
an internal pressure calculation unit for calibration adapted to calculate the internal pressure of the applied load measurement unit for calibration using the load detected by the load detecting unit for calibration and internal pressure calculation data for calibration in the device attached state before collection of the biological component; and
a correction unit adapted to correct the internal pressure calculation data using the internal pressure calculated by the internal pressure calculation unit for calibration;
wherein the internal pressure calculation data for calibration is data indicative of a relationship between the load detected by the load detecting unit for calibration and the internal pressure of the applied load measurement unit for calibration; and
the internal pressure calculation unit for calibration performs a calculation reflecting a change in the internal pressure calculation data for calibration due to temperature.

10. A circuit internal pressure acquisition method using a biological component collection system equipped with a separation device adapted to separate a biological component from a biological liquid, and a biological component collection device configured to be attachable to the separation device and collect a desired biological component from the biological liquid;
wherein the biological component collection device includes a line forming member comprised of a deformable polymer comprised of vinyl chloride, polyolefin, or polyurethane, and forming a biological liquid line to allow the biological liquid or the biological component to flow therein;
the circuit internal pressure acquisition method comprising:
a load detecting step of detecting a load applied to an applied load measurement unit which partially makes up the line forming member in a device attached state in which the biological component collection device is attached to the separation device;
a temperature measurement acquiring step of acquiring temperature measurements by a temperature acquisition unit, during collection of the biological component by which the biological liquid or the biological component is made to flow through the biological liquid line in the device attached state; and an internal pressure calculation step of calculating an internal pressure of said applied load measurement unit, using the load detected in said load detecting step and internal pressure calculation data based on said temperature measurements;

wherein the internal pressure calculation data is data indicative of a relationship between the load detected by the load detecting unit and the internal pressure of the applied load measurement unit; and in the internal pressure calculation step, a calculation is performed reflecting a change in the internal pressure calculation data depending on temperature wherein:

the internal pressure calculation data includes a reaction force of the applied load measurement unit; and in the internal pressure calculation step, when calculating the internal pressure of the applied load measurement unit, a calculation is performed reflecting a change in the reaction force of the applied load measurement unit due to temperature.

11. The circuit internal pressure acquisition method according to claim 10, further comprising:

an information acquisition step of acquiring influence information that exerts an influence on the reaction force of the applied load measurement unit; and in the internal pressure calculation step, a calculation is performed reflecting the change in the reaction force of the applied load measurement unit due to temperature, on the basis of the influence information acquired in the information acquisition step.

12. The circuit internal pressure method according to claim 11, wherein:

the biological component collection device includes a hollow portion forming member comprised of a deformable polymer comprised of vinyl chloride, polyolefin, or polyurethane, and which forms a hollow portion through which the biological liquid and the biological component do not flow during operation of the separation device; and the internal pressure acquisition method comprising:

a reaction force detecting step of detecting a reaction force of an applied reaction force measurement unit that makes up a portion of the hollow portion forming member, in order to obtain the reaction force of the applied load measurement unit which changes in accordance with a time period during collection of the biological component in the device attached state; and a reaction force correction step of correcting the reaction force detected in the reaction force detecting step using the influence information acquired in the information acquisition step;

wherein, in the internal pressure calculation step, the internal pressure of the applied load measurement unit is calculated using the reaction force corrected in the reaction force correction step.

13. The circuit internal pressure acquisition method according to claim 11, further comprising:

a data acquisition step of acquiring initial data indicative of a temporal change in the reaction force of the applied load measurement unit using the load detected by the load detecting step in the device attached state before collection of the biological component;

an estimated data calculation step of calculating, on a basis of the initial data, estimated data for predicting the reaction force of the applied load measurement unit which changes in accordance with the time period during collection of the biological component;

a reaction force calculation step of calculating the reaction force of the applied load measurement unit using the estimated data during collection of the biological component; and a reaction force correction step of correcting the reaction force calculated in the reaction force calculation step using the influence information acquired in the information acquisition step;

wherein, in the internal pressure calculation step, the internal pressure of the applied load measurement unit is calculated using the reaction force corrected in the reaction force correction step.

\* \* \* \* \*